(12) United States Patent
King et al.

(10) Patent No.: US 8,931,950 B2
(45) Date of Patent: Jan. 13, 2015

(54) DEVICE FOR CALORIMETRIC MEASUREMENT

(75) Inventors: William P. King, Champaign, IL (US); Jungchul Lee, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 468 days.

(21) Appl. No.: 13/059,812

(22) PCT Filed: Aug. 20, 2009

(86) PCT No.: PCT/US2009/054539
§ 371 (c)(1),
(2), (4) Date: Apr. 15, 2011

(87) PCT Pub. No.: WO2010/022285
PCT Pub. Date: Feb. 25, 2010

(65) Prior Publication Data
US 2011/0268148 A1    Nov. 3, 2011

Related U.S. Application Data

(60) Provisional application No. 61/090,449, filed on Aug. 20, 2008.

(51) Int. Cl.
*G01K 17/00* (2006.01)
*G01N 25/22* (2006.01)
*G01N 25/48* (2006.01)

(52) U.S. Cl.
CPC .......... *G01K 17/006* (2013.01); *G01N 25/4813* (2013.01); *Y10S 977/902* (2013.01)
USPC ............. 374/36; 374/178; 374/144; 374/121; 422/51; 422/31; 436/147; 977/902

(58) Field of Classification Search
CPC ............................. G01K 17/006; H03B 19/18
USPC ............ 374/31–39, 178, 4, 5, 120, 121, 141, 374/144; 422/51; 436/147; 977/902, 742
See application file for complete search history.

(56) References Cited

U.S. PATENT DOCUMENTS 4,166,269 A    8/1979    Stephens et al.
5,264,375 A *  11/1993    Bang et al. .................... 505/330
(Continued)

FOREIGN PATENT DOCUMENTS

DE    4338891 A1 *  9/1994
EP     262601 A *  4/1988
(Continued)

OTHER PUBLICATIONS

Abedinov et al. (Nov./Dec. 2001) "Micromachined Piezoresistive Cantilever Array With Integrated Resistive Microheater for Calorimetry and Mass Detection," *J. Vac. Sci. Technol. A* 19(6):2884-2888.
(Continued)

*Primary Examiner* — Gail Kaplan Verbitsky
(74) *Attorney, Agent, or Firm* — Lathrop & Gage LLP

(57) ABSTRACT

In one aspect, provided herein is a single crystal silicon microcalorimeter, for example useful for high temperature operation and long-term stability of calorimetric measurements. Microcalorimeters described herein include microcalorimeter embodiments having a suspended structure and comprising single crystal silicon. Also provided herein are methods for making calorimetric measurements, for example, on small quantities of materials or for determining the energy content of combustible material having an unknown composition.

19 Claims, 19 Drawing Sheets

(56) References Cited

U.S. PATENT DOCUMENTS

| | | | |
|---|---|---|---|
| 5,345,815 A | 9/1994 | Albrecht et al. | |
| 5,386,720 A | 2/1995 | Toda et al. | |
| 5,441,343 A | 8/1995 | Pylkki et al. | |
| 5,444,244 A | 8/1995 | Kirk et al. | |
| 5,451,371 A | 9/1995 | Zanni-Fisher et al. | |
| 5,464,966 A | 11/1995 | Gaitan et al. | |
| 5,468,959 A | 11/1995 | Tohda et al. | |
| 5,583,286 A | 12/1996 | Matsuyama | |
| 5,600,174 A * | 2/1997 | Reay et al. | 257/467 |
| 5,726,073 A * | 3/1998 | Zhang et al. | 438/20 |
| 5,801,070 A | 9/1998 | Zanini-Fisher et al. | |
| 5,929,438 A | 7/1999 | Suzuki et al. | |
| 5,936,237 A | 8/1999 | van der Weide | |
| 5,969,238 A | 10/1999 | Fischer | |
| RE36,488 E | 1/2000 | Elings et al. | |
| 6,050,722 A | 4/2000 | Thundat et al. | |
| 6,073,485 A | 6/2000 | Kitamura | |
| 6,079,255 A | 6/2000 | Binnig et al. | |
| 6,094,971 A | 8/2000 | Edwards et al. | |
| 6,096,559 A | 8/2000 | Thundat et al. | |
| 6,097,197 A | 8/2000 | Matsuyama et al. | |
| 6,233,206 B1 | 5/2001 | Hamann et al. | |
| 6,383,823 B1 | 5/2002 | Takahashi et al. | |
| 6,436,346 B1 | 8/2002 | Doktycz et al. | |
| 6,452,170 B1 | 9/2002 | Zypman et al. | |
| 6,467,951 B1 | 10/2002 | Ghoshal | |
| 6,487,515 B1 | 11/2002 | Ghoshal | |
| 6,535,824 B1 | 3/2003 | Mansky et al. | |
| 6,583,412 B2 | 6/2003 | Williams | |
| 6,648,503 B2 * | 11/2003 | Tanaka et al. | 374/31 |
| 6,667,467 B2 | 12/2003 | Shimizu et al. | |
| 6,668,627 B2 | 12/2003 | Lanage et al. | |
| 6,727,778 B2 * | 4/2004 | Kudrle et al. | 333/33 |
| 6,762,402 B2 | 7/2004 | Choi et al. | |
| 6,763,705 B1 | 7/2004 | Thundat et al. | |
| 6,785,041 B1 | 8/2004 | Vodopyanov | |
| 6,862,923 B2 | 3/2005 | Buguin et al. | |
| 6,865,044 B1 | 3/2005 | Albrecht et al. | |
| 6,875,269 B2 * | 4/2005 | Hartmann et al. | 117/13 |
| 6,880,386 B1 | 4/2005 | Krotil et al. | |
| 6,893,884 B2 | 5/2005 | Shi et al. | |
| 6,894,272 B2 | 5/2005 | Kranz et al. | |
| 6,930,502 B2 | 8/2005 | Lee et al. | |
| 6,932,504 B2 | 8/2005 | Takahashi et al. | |
| 6,935,167 B1 | 8/2005 | Sahin et al. | |
| 6,983,644 B2 | 1/2006 | Yamanaka et al. | |
| 6,983,653 B2 * | 1/2006 | Iwaki et al. | 73/204.23 |
| 7,033,840 B1 * | 4/2006 | Tagge et al. | 436/147 |
| 7,038,996 B2 | 5/2006 | Binnig et al. | |
| 7,074,340 B2 | 7/2006 | Lugstein et al. | |
| 7,104,113 B2 * | 9/2006 | Zribi et al. | 73/31.05 |
| 7,129,486 B2 | 10/2006 | Spizig et al. | |
| 7,155,964 B2 | 1/2007 | Huang et al. | |
| 7,168,298 B1 | 1/2007 | Manginell et al. | |
| 7,208,730 B2 | 4/2007 | Berstis | |
| 7,211,789 B2 | 5/2007 | Berstis | |
| 7,260,980 B2 | 8/2007 | Adams et al. | |
| 7,261,461 B2 | 8/2007 | Grudin et al. | |
| 7,268,348 B2 | 9/2007 | Binning et al. | |
| 7,281,419 B2 | 10/2007 | Wang et al. | |
| 7,291,466 B2 | 11/2007 | Su et al. | |
| 7,404,314 B2 | 7/2008 | Sahin et al. | |
| 7,451,638 B1 | 11/2008 | Sahin et al. | |
| 7,497,613 B2 | 3/2009 | King et al. | |
| 7,521,257 B2 | 4/2009 | Adams et al. | |
| 7,677,088 B2 | 3/2010 | King | |
| 7,741,615 B2 | 6/2010 | Putterman et al. | |
| 7,877,816 B2 | 1/2011 | Spizig et al. | |
| 7,928,343 B2 * | 4/2011 | King et al. | 219/444.1 |
| 8,001,830 B2 | 8/2011 | Dazzi et al. | |
| 8,093,715 B2 * | 1/2012 | Xu et al. | 257/720 |
| 8,719,960 B2 * | 5/2014 | King | 850/40 |
| 2003/0101006 A1 * | 5/2003 | Mansky et al. | 702/30 |
| 2004/0020279 A1 | 2/2004 | Degertekin et al. | |
| 2004/0195096 A1 | 10/2004 | Tsamis et al. | |
| 2004/0223884 A1 | 11/2004 | Chen et al. | |
| 2004/0228258 A1 | 11/2004 | Binnig et al. | |
| 2005/0109081 A1 * | 5/2005 | Zribi et al. | 73/31.05 |
| 2005/0127926 A1 | 6/2005 | Lee et al. | |
| 2005/0164299 A1 | 7/2005 | Stewart | |
| 2006/0032289 A1 | 2/2006 | Pinnaduwage et al. | |
| 2006/0040057 A1 | 2/2006 | Sheehan et al. | |
| 2006/0150720 A1 | 7/2006 | Nakayama et al. | |
| 2006/0207317 A1 | 9/2006 | Watanabe | |
| 2006/0222047 A1 | 10/2006 | Reading | |
| 2006/0238206 A1 | 10/2006 | Eng et al. | |
| 2006/0254345 A1 | 11/2006 | King et al. | |
| 2006/0289510 A1 | 12/2006 | Atkins et al. | |
| 2007/0012094 A1 | 1/2007 | Degertekin et al. | |
| 2007/0063141 A1 | 3/2007 | Duerig et al. | |
| 2007/0103697 A1 | 5/2007 | Degertekin | |
| 2007/0107502 A1 | 5/2007 | Degertekin | |
| 2007/0109091 A1 | 5/2007 | Landsberger et al. | |
| 2007/0114401 A1 | 5/2007 | King et al. | |
| 2007/0125753 A1 | 6/2007 | Fink et al. | |
| 2007/0189920 A1 | 8/2007 | Gimzewski | |
| 2007/0190562 A1 | 8/2007 | Berstis | |
| 2007/0286254 A1 | 12/2007 | Fon et al. | |
| 2007/0295064 A1 | 12/2007 | Degertekin et al. | |
| 2007/0298551 A1 * | 12/2007 | Bouvet et al. | 438/151 |
| 2008/0093226 A1 | 4/2008 | Briman et al. | |
| 2008/0179713 A1 * | 7/2008 | Landsberger et al. | 257/633 |
| 2008/0283755 A1 | 11/2008 | Dazzi et al. | |
| 2008/0295583 A1 | 12/2008 | Giessibl | |
| 2008/0307865 A1 | 12/2008 | Degertekin | |
| 2009/0013770 A1 | 1/2009 | Proksche et al. | |
| 2009/0056428 A1 | 3/2009 | King et al. | |
| 2009/0139340 A1 | 6/2009 | King et al. | |
| 2009/0249521 A1 | 10/2009 | Dazzi et al. | |
| 2010/0078753 A1 * | 4/2010 | Mehregany et al. | 257/467 |
| 2011/0030109 A1 | 2/2011 | Saito | |
| 2011/0056428 A1 * | 3/2011 | Uto et al. | 117/35 |
| 2011/0061452 A1 | 3/2011 | King et al. | |
| 2011/0078834 A1 | 3/2011 | King | |
| 2011/0126329 A1 | 5/2011 | Despont et al. | |
| 2011/0154546 A1 | 6/2011 | Proksch et al. | |
| 2011/0167524 A1 | 7/2011 | Hu et al. | |

FOREIGN PATENT DOCUMENTS

| | | | |
|---|---|---|---|
| JP | 01201147 A * | 8/1989 | |
| JP | 09210684 A * | 8/1997 | |
| JP | 2003215095 A * | 7/2003 | |
| WO | WO94/10822 | 5/1994 | |
| WO | WO 03/011747 | 2/2003 | |
| WO | WO 2006/046924 | 5/2006 | |
| WO | WO 2006/073426 | 7/2006 | |
| WO | WO 2006/107991 | 11/2006 | |
| WO | WO 2007/011364 | 1/2007 | |
| WO | WO 2007/026177 | 3/2007 | |
| WO | WO 2008/143817 | 11/2008 | |
| WO | WO 2009/097487 | 8/2009 | |
| WO | WO 2010/022285 | 2/2010 | |
| WO | WO 01/20283 | 3/2011 | |

OTHER PUBLICATIONS

Abel et al. (Jun. 2007) "Thermal Metrology of Silicon Microstructures Using Raman Spectroscopy," *IEEE Trans. Comp. Pack. Tech.* 30(2):200-208.

Akiyama et al. (Nov./Dec. 2000) "Integrated Atomic Force Microscopy Array Probe with Metal-Oxide-Semiconductor Field Effect Transistor Stress Sensor, Thermal Bimorph Actuator, and On-Chip Complementary Metal-Oxide-Semiconductor Electronics," *J. Vac. Sci. Technol. B* 18(6):2669-2675.

Albright et al. (Apr. 1999) "'True' Temperature Measurements on Microscope Semiconductor Targets," In: SPIE Conference on Thermosense XXI, Orlando, Florida, SPIE 3700:245-250.

Allen et al. (1998) "MEMS-Based Scanning Calorimeter for Thermodynamic Properties of Nanostructures," *Microscale Thermophys. Eng.* 2:11-19.

(56) References Cited

OTHER PUBLICATIONS

Asano et al. (Sep. 1992) "Field-Excited Electron Emission from Ferroelectric Ceramic in Vacuum," *Jpn. J. Appl. Phys.* 31(9B):3098-3101.

Auciello et al. (1995) "Low Voltage Electron Emission from Pb($Zr_xTi_{1-x}$)$O_3$-Based Thin Film Cathodes," *Appl. Phys. Lett.* 66:2183-2185.

Beckel et al. (Mar. 30, 2007) "Micro-Hotplates—A Platform for Micro-Solid Oxide Fuel Cells," *J. Power Sources* 166:143-148.

Belmonte et al. (Apr. 26, 2006) "High-Temperature Low-Power Performing Micromachined Suspended Micro-Hotplate for Gas sensing Applications," *Sens. Actuators B. Chem.* 114:826-835.

Berger et al. (1998) "Micromechanical Thermogravimetry," *Chem. Phys. Lett.* 294:363-369.

Berger et al. (Jul. 1, 1996) "Thermal Analysis Using a Micromechanical Calorimeter," *Appl. Phys. Lett.* 69(1):40-42.

Beyder et al. (2006) "Reducing Probe Dependent Drift in Atomic Force Microscope with Symmetrically Supported Torsion Levers," *Rev. Sci. Instrum.* 77:056105.

Bhatia et al. (2011) "High-Temperature Piezoresponse Force Microscopy," *Appl. Phys. Lett.* 99:173103.

Bian et al. (2007) "Electron Emission from $SrTiO_3$-Coated Silicon-Tip Arrays," *J. Vac. Sci. Technol. B* 21:817-821.

Bian et al. (2009) "Field Emission Properties of Si Tip Arrays Coated with N-Doped $SrTiO_3$ Thin Films at Different Substrate Temperature," *J. Appl. Phys.* 105:013312.

Binnig et al. (Mar. 3, 1986) "Atomic Force Microscope," *Phys. Rev. Lett.* 56(9):930-933.

Binnig et al. (Mar. 1, 1999) "Ultrahigh-Density Atomic Force Microscopy Data Storage with Erase Capability," *Appl. Phys. Lett.* 74(9):1329-1331.

Biswal et al. (2006) "Nanomechanical Detection of DNA Melting on Microcantilever Surfaces," *Anal. Chem.* 78:7104-7109.

Biswal et al. (2007) "Using a Microcantilever Array for Detecting Phase Transitions and Stability of DNA," *Clin. Lab. Med.* 27:163-171.

Biswal et al. (Aug. 2006) "Using a Microcantilever Array for Detecting Phase Transitions and Stability of DNA," *J. Assoc. Lab. Auto.* 11:222-226.

Boisen et al. (2000) "Environmental Sensors Based on Micromachined Cantilevers with Integrated Read-Out," *Ultramicroscopy* 82:11-16.

Brown et al. (May 1999) "Cantilever-in-Cantilever Micromachined Pressure Sensors Fabricated in CMOS Technology," *Proc. 1999 IEEE Can. Conf. on Elec. and Comp. Eng.* :1686-1691.

Buguin et al. (May 7, 2001) "Active Atomic Force Microscopy Cantilevers for Imaging in Liquids," *Appl. Phys. Lett.* 78(19):2982-2984.

Butt et al. (1995) "Calculation of Thermal Noise in Atomic Force Microscopy," *Nanotechnology* 6(1):1-7.

Byer et al. (1972) "Pyroelectric Coefficient Direct Measurement Technique and Application to a nsec Response Time Detector," *Ferroelectrics* 3:333-338.

Cahill, D.G. (1990) "Thermal Conductivity Measurement from 30 to 750K: The 3ω Method," *Rev. Sci. Instrum.* 61(2):802-808.

Cavicchi et all. (Jan. 1, 2004) "Micro-Differential Scanning Calorimeter for Combustible Gas Sensing," *Sens. Actuators B. Chem.* 97:22-30.

Chandra et al. (2007) "A Landau Primer for Ferroelectrics," In; *Physics of Ferroelectrics, Spring Topics in Applied Physics* 105:69-.

Chen et al. (Aug. 1994) "Resonance Response of Scanning Force Microscopy Cantilevers," *Rev. Sci. Instrum.* 65(8):2532-2537.

Chen et al. (May 2008) "Si Field Emitter Arrays Coated with Thin Ferroelectric Films," *Ceram. Int.* 34:971-977.

Choi et al. (2004) "Enhancement of Ferroelectricity in Strained $BaTiO_3$ Thin Films," *Science* 306:1005-1009.

Chu et al. (2006) "Nanoscale Domain Control in Multiferroic $BiFeO_3$ Thin Films," *Adv. Mater.* 18:2307-2311.

Chu et al. (2007) "Domain Control in Multiferroic $BiFeO_3$ Through Substrate Vicinality," *Adv. Mater.* 19:2662-2666.

Chu et al. (2008) "Electric-Field Control of Local Ferromagnetism Using a Magnetoelectric Multiferroic," *Nature Mater.* 7:478.

Chu et al. (2009) "Nanoscale Control of Domain Architectures in $BiFeO_3$ Thin Films," *Nano Lett.* 9:1726-1730.

Chui et al. (Oct. 28, 1996) "Low-Stiffness Silicon Cantilevers for Thermal Writing and Peizoresistive Readback with Atomic Force Microscope," *Appl. Phys. Lett.* 69(18):2767-2769.

Chui et al. (1999) "Intrinsic-Carrier Thermal Runaway in Silicon Microcantilevers," *Microscale Thermophys. Eng.* 3:217-228.

Chui et al. (2007) "Advanced Temperature Compensation for Piezoresistive Sensors Based on Crystallographic Orientation," *Rev. Sci. Instrum.* 78:043706.

Chui et al. (Mar. 1998) "Low-Stiffness Silicon Cantilevers with Integrated Heaters and Piezoresistive Sensors for High-Density AFM Thermomechanical Data Storage," *J. Microelectromech. Syst.* 7(1):69-78.

Dames et al. (2005) "1ω, 2ω, and 3ω Methods for Measurements of Thermal Properties," *Rev. Sci. Instrum.* 76(12):124902.

Damodaran et al. (2011) "Nanoscale Structure and Mechanism for Enhanced Electromechanical Response of Highly-Strained $BiFeO_3$ Thin Films," *Adv. Mater.* 23:3170-3175.

Datskos (1996) "Remote Infrared Radiation Detection Using Piezoresistive Microcantilevers," *Appl. Phys. Lett.* 69: 2986-2988.

Dazzi (2008) "Sub-100nm Infrared Spectroscopy and Imaging based on a near-field photo-thermal technique ("PTIR")," in Biomedical vibrational spectroscopy, J. Wiley ed., 291.

Dazzi et al. (2004) "Theoretical Study of an Absorbing Sample in Infrared Near-Field Spectromicroscopy," *Optics Comm.* 235:351-360.

Dazzi et al. (Sep. 5, 2005) "Local Infrared Microspectroscopy with Subwavelength Spatial Resolution with an Atomic Force Microscope Tip used as a Photothermal Sensor," *Optics Lett.* 30(18):2388-2390.

Dazzi et al. (2006) "Subwavelength Infrared Spectromicroscopy using an AFM as a Local Absorption Sensor," *Infrared Phys. Technol.* 49:113-121.

Dazzi et al. (2007) "Analysis of Nano-Chemical Mapping Performed by an AFM-Based ("AFMIR") Acousto-Optic Technique," *Ultramicroscopy* 107(12):1194-1200.

Degamber et al. (Sep. 2004) "Simultaneous DSC/FTIRS/TMA," *Meas. Sci. Technol.* 15:L5-L10.

Denlinger et al. (Apr. 1994) "Thin-Film Microcalorimeter for Heat-Capacity Measurements from 1.5K to 800K," *Rev. Sci. Instrum.* 65:946-958.

Despont et al. (2000) "VLSI-NEMS Chip for Parallel AFM Data Storage," *Sens. Actuators A* 80:100-107.

Dreschler et al. (2003) "Cantilevers with Nano-Heaters for Thermomechanical Storage Application," *Microelectr. Eng.* 67/68:397-404.

Dücsö et al. (May 1997) "Porous Silicon Bulk Micromachining for Thermally Isolated Membrane Formation," *Sens. Actuators A Phys.* 60:235-239.

Dunaevsky et al. (Jun. 15, 1999) "Electron/Ion Emission from the Plasma Formed on the Surface of Ferroelectrics. I. Studies of Plasma Parameters without Applying and Extracting Voltage," *J. Appl. Phys.* 85(12):8464-8473.

Efremov et al. (Jan. 2004) "Ultrasensitive, Fast, Thin-Film Differential Scanning Calorimeter," *Rev. Sci. Instrum.* 75(1):179-191.

Efremov et al. (Aug. 22, 2003) "Glass Transition in Ultrathin Polymer Films: Calorimetric Study," *Phys. Rev. Lett.* 91(8):085703.

Efremov et al. (Feb. 26, 2002) "Thin-Film Differential Scanning Calorimetry: A New Probe for Assignment of the Glass Transition of Ultrathin Polymer Films," *Macromolecules* 35(5):1481-1483.

Efremov et al. (Jun. 26, 2003) "Glass Transition of Thin Films of Poly(2-Vinyl Pyridine) and Poly(Methyls Methacrylate): Nanocalorimetry Measurements," *Thermochim Acta* 403:37-41.

Efrimov et al. (Jun. 15, 2004) "Probing Glass Transition of Ultrathin Polymer Films at a Time Scale of Seconds Using Fast Differential Scanning Calorimetry," *Macromolecules* 37:4607-4616.

Enders et al. (2004) "Lorentz-Force-Induced Excitation of Cantilevers for Oscillation-Mode Scanning Probe Microscopy," *Surf. Interface Anal.* 36(2):119-123.

(56) References Cited

OTHER PUBLICATIONS

Felts et al. (2009) "Mechanical Design for Tailoring Resonance Harmonics of an Atomic Force Microscope Cantilever During Tip-Surface Contact," *J. Micromech. Microeng.* 19: 115008.
Fernando et al. (2007) "Improved Cantilever Profiles for Sensor Elements," *J. Phys. D-Appl. Phys.* 40(24):7652-7655.
French, P.J. (2002) "Polysilicon: A Versatile Material for Microsystems," *Sens. Actuators A* 99:3-12.
Frisbie et al. (Sep. 30, 1994) "Functional Group Imaging by Chemical Force Microscopy," *Science* 265:2071-2074.
Fritz et al. (Apr. 14, 2000) "Translating Biomolecular Recognition into Nanomechanics," *Science* 288:316-318.
Fung et al. (Jun. 1996) "Thermal Analysis and Design of a Micro-Hotplate for Integrated Gas-Sensor Applications," *Sens. Actuators A Phys.* 54:482-487.
Fürjes et al. (2004) "Thermal Characterization of Micro-Hotplates Used in Sensor Structures," *Superlattices Microstruct.* 35:455-464.
Fürjes et al. (Apr. 30, 2002) "Thermal Investigation of Micro-Filament Heaters," *Sens. Actuators A. Phys.* 99:98-103.
Fürjes et al. (Jul. 2002) "Materials and Processing for Realization of Micro-Hotplates Operated at Elevated Temperature," *J. Micromech. Microeng.* 12:425-429.
Gimzewski et al. (Jan. 28, 1994) "Observation of a Chemical Reaction Using a Micromechanical Sensor," *Chem. Phys. Lett.* 217(5-6):589-594.
Goericke et al. (2007) "Microcantilever Hotplates with Temperature-Compensated Peizoresistive Strain Sensors," *Sens. Actuators A* 143(2):181-190.
Gotsmann et al. (Web Release Jan. 17, 2004) "Thermally Activated Nanowear Models of a Polymer Surface Induced by a Heated Tip," *Langmuir* 20:1495-1500.
Gotsmann et al. (2005) "Experimental Observation of Attractive and Repulsive Thermal Forces on Microcantilevers," *Appl. Phys. Lett.* 87:194102.
Graf et al. (Jan. 2005) "3D Nonlinear Modeling of Microhotplates in CMOS Technology for Use as Metal-Oxide-Based Gas Sensors," *J. Micromech. Microeng.* 15:190-200.
Gruverman (1996) "Scanning Force Microscopy for the Study of Domain Structure in Ferroelectric Thin Films," *J Vac. Sci. Technol. B: Microelectron. Nanometer Struct.* 14(2):602-605.
Gundel et al. (1989) "Copious Electron Emission from PLZT Ceramics with High Zirconium Concentration," *Ferroelectrics* 100:1-16.
Gundel et al. (1990) "Electric Field-Excited Electron Emission from PLZT-X/65/35 Ceramics," *Ferroelectrics* 110:183-192.
Gundel et al. (Jan. 1991) "Time-Dependent Electron Emission frrom Ferroelectrics by External Pulsed Electric Fields," *J. Appl. Phys.* 69(2):975-982.
Guo et al. (Jan. 2007) "A Monolithic Integrated 4×4 Tin Oxide Gas Sensor Array with On-Chip Multiplexing and Differential Readout Circuits," *Solid-State Electron.* 51:69-76.
Hagleitner et al. (Nov. 15, 2001) "Smart Single-Chip Gas Sensor Microsystem," *Nature* 414:293-296.
Hammiche et al. (Feb. 2004) "Progress in Near-Field Photothermal Infra-Red Microscopy," *J. Microscopy* 213(2):129-134.
Han et al. (2005) "A Novel Temperature-Compensating Structure for Micromechanical Bridge Resonator," *J. Micromech. Microeng.* 15: 702-705.
Han et al. (May 17, 2005) "Size Effect on Heat Transfer in Micro Gas Sensors," *Sens. Actuators A Phys.* 120:397-402.
Hey et al. (1997) "A Combined Differential Scanning Calorimeter Optical Video Microscope for Crystallization Studies," *J. Therm. Anal.* 49:991-998.
Higa et al. (1998) "Gated Si Field Emitter Array Prepared by Using Anodization," *J. Wac. Sci. Technol. B* 16(2):651-653.
Hii et al. (2006) "Characterizing Field Emission from Individual Carbon Nanotubes at Small Distances," *J. Vac. Sci. Technol. B* 24(3):1081-1087.
Hodges (Oct. 2001) "Improved Atomic Force Microscope Cantilever Performance by Ion Beam Modification," *Rev. Sci. Instrum.* 72(10):3880-3883.
Holbery et al. (Oct. 2000) "Experimental Determination of Scanning Probe Microscope Cantilever Spring Constants Utilizing a Nanoindentation Apparatus," *Rev. Sci. Instrum.* 71(10):3769-3776.
Hotovy et al. (Apr. 2008) "Gallium Arsenide Suspended Microheater for MEMS Sensor Arrays," *Microsyst. Tech.* 14:629-635.
Hsu et al. (Feb. 6, 2004) "Cubic AgPbmSbTe2+m: Bulk Thermoelectric Materials with High Figure of Merit," *Science* 303:818-821.
Hu et al. (2008) "Investigation of the Natural Convection Boundary Condition in Microfabricated Structures," *Int. J. Therm. Sci.* 47:820-824.
Huijben et al. (2008) "Critical Thickness and Orbital Ordering in Ultrathin $La_{0.7}Sr_{0.3}MnO_3$ Films," *Phys. Rev. B* 78:094413.
Huiling (2008) "Concentrated-Mass Cantilever Enhances Multiple Harmonics in Tapping Mode Atomic Force Microscopy," *Appl. Phys. Lett.* 92(15):151903.
Hull (1999) "Electrical Properties," and "Implantation/ Irradiation of Silicon," In; *Properties of Crystalline Silicon*, Ch. 8 and 14, INSPEC, London pp. 411-475 and 731-773.
Hutter et al. (Jul. 1993) "Calibration of Atomic-Force Microsope Tips," *Rev. Sci. Instrum.* 64(7):1869-1873.
International Search Report and Written Opinion, Corresponding to International Application No. PCT/US09/32545, Mailed Apr. 9, 2009.
International Search Report and Written Opinion, Corresponding to International Application No. PCT/US09/54539, Mailed Dec. 23, 2009.
Ivers et al. (1993) "Electron-Beam Diodes Using Ferroelectric Cathodes," *J. Appl. Phys.* 73(6):2667-2671.
Jensen et al. (2010) "Emittance of a Field Emission Electron Source," *J. Appl. Phys.* 107:014903.
Jensenius et al. (May 1, 2000) "A Microcantilever-Based Alcohol Vapor Sensor-Application and Response Model," *Appl. Phys. Lett.* 76(18):2615-2617.
Johnson et al. (Jan. 17, 1992) "Applications of Simultaneous DSC/FTIR Analysis," *Thermochim. Acta* 195:5-20.
Kang et al. (2003) "Effect of Annealing Temperature on the Electron Emission Characteristics of Silicon Tips Coated with $Ba_{0.67}Sr_{0.33}TiO_3$ Thin Film," *J. Vac. Sci. Technol. B* 21(1):453-457.
Kang et al. (May/Jun. 2001) "Electron Emission from Silicon Tips Coated with Sol-Gel $(Ba_{0.67}Sr_{0.33})TiO_3$ Ferroelelctric Thin Film," *J. Vac. Sci. Technol. B* 19(3):1073-1076.
Kim et al. (2007) "Nanotopographical Imaging Using a Heated Atomic Force Microscope Cantilever Probe," *Sens. Actuators A* 136:95-103.
Kim et al. (Jun. 2009) "Thermal Conduction Between a Heated Microcantilever and a Surrounding Air Environment," *Appl. Therm. Eng.* 29(8-9):1631-1641.
King et al. (2006) "Nanoscale Thermal Analysis of an Energetic Material," *Nano Lett.* 6(9):2145-2149.
King et al. (Dec. 2002) "Design of Atomic Force Microscope Cantilevers for Combined Thermomechanical Writing and Thermal Reading in Array Operation," *J. Microelectromech. Syst.* 11(6):765-774.
King et al. (Feb. 26, 2001) "Atomic Force Microscope Cantilevers for Combined Thermomechanical Data Writing and Reading," *Appl. Phys. Lett.* 78(9):1300-1302.
Krasik et al. (Feb. 2003) "Ferroelectric Plasma Sources and Their Applications," IEEE *Trans. Plasma Sci.* 31(1):49-59.
Krebs et al. (1993) "A Low-Power Integrated Catalytic Gas Sensor," Sens. Actuators B 13/14:1155-1158.
Laconte et al. (Oct. 2004) "SOI CMOS Compatible Low-Power Microheater Optimization for the Fabrication of Smart Gas Sensors," *IEEE Sens. J.* 4(5):670-680.
Lai et al. (Aug. 28, 1995) "High-Speed ($10^{4\circ}$ C./s) Scanning Microcalorimetry with Monolayer Sensitivity (J/m2)," *Appl. Phys. Lett.* 67(9):1229-1231.
Lai et al. (Jul. 1, 1996) "Size-Dependent Melting Properties of Small Tin Particles: Nanocalorimetric Measurements," *Phys. Rev. Lett.* 77(1):99-102.
Lai et al. (Mar. 2, 1998) "Melting Point Depression of Al Clusters Generated During the Early Stages of Film Growth: Nanocalorimetry Measurements," *Appl. Phys. Lett.*72(9):1098-1100.
Lang et al. (Aug. 2005) "Pyroelectricity: From Ancient Curiosity to Modern Imaging Tool," *Phys. Today* :31-36.

(56) References Cited

OTHER PUBLICATIONS

Lee et al. (1998) "Fabrication and Characterization of Silicon Field Emitter Arrays by Spin-On-Glass Etch Back," *J. Vac. Sci. Technol. B* 16(1):238-241.

Lee et al. (2003) "Classifying Combustible Gases Using Microgas Sensor Array," *Sens. Actuators B* 93:1-6.

Lee et al. (2007) "Characterization of Liquid and Gaseous Micro- and Nanojets using Microcantilever Sensors," *Sens. Actuators A* 134:128-139.

Lee et al. (2007) "Microcantilever Hotplates: Design, Fabrication, and Characterization," *Sens. Actuators A* 136:291-298.

Lee et al. (2007) "Thermal Conduction from Microcantilever Heaters in Partial Vacuum," *J. Appl. Phys.* 101:14906.

Lee et al. (2007) "Microcantilever Actuation via Periodic Internal Heating," *Rev. Sci. Instrum.* 78(12):126102.

Lee et al. (Nov. 2008) "Liquid Operation of Silicon Microcantilever Heaters," *IEEE Sens. J.* 8(11):1805-1806.

Lee et al. (2008) "Microthermogravimetry Using a Microcantilever Hot Plate with Integrated Temperature-Compensated Piezoresistive Strain Sensors," *Rev. Sci. Instrum.* 79:054901.

Lee et al. (2008) "Phase Change and Cooling Characteristics of Microjets Measured using Microcantilever Heaters," *Sens. Actuators A* 147:64-69.

Lee et al. (Dec. 2006) "Electrical, Thermal, and Mechanical Characterization of Silicon Microcantilever Heaters," *J. Microelectromech. Syst.* 15(6):1644-1655.

Lee et al. (Dec. 2008) "Differential Scanning Calorimeter Based on Suspended Membrane Single Crystal Silicon Microhotplate," *J. Microelectromechanical Syst.* 17(6):1513-1525.

Lee et al. (Mar. 15, 2002) "A Microsensor Array with Porous Tin Oxide Thin Films and Microhotplate Dangled by Wires in Air," *Sens. Actuators B Chem.* 83:250-255.

Lee et al. (May 2007) "Fabrication, Characterization and Application of Multifunctional Microcantilever Heaters," Ph.D. Dissertation, Georgia Institute of Technology.

Li et al. (2008) "Concentrated-Mass Cantilever Enhances Multiple Harmonics in Tapping-Mode Atomic Force Microscopy," *Appl. Phys. Lett.* 92(15):151903.

Lu et al. (2007) "Field Emission of Silicon Emitter Arrays Coated with Sol-Gel $(Ba_{0.65}Sr_{0.35})_{1-x}La_xTiO_3$ Thin Films," *J. Appl. Phys.* 102:014113.

Lutwyche et al. (1999) "5×5 2D AFM Cantilever Arrays a First Step Towards a Terabit Storage Device," *Sens. Actuators A* 73:89-94.

Lyeo et al. (Feb. 6, 2004) "Profiling the Thermoelectric Power of Semiconductor Junctions with Nanometer Resolution," *Science,* 303:816-818.

Maali et al. (2006) "Reduction of the Cantilever Hydrodynamic Damping Near a Surface by Ion-Beam Milling," *J. Appl. Phys.* 99(2):024908.

Madou (1997) "Wet Bulk Micromachining," and "Microfabrication Applications," In Fundamentals of Microfabrication, Ch. 4 and 10, CRC Press, Boca Raton, Florida, pp. 145-215 and 449-514.

Mamin, H.J. (1996) "Thermal Writing Using a Heated Atomic Force Microscope Tip," *Appl. Phys. Lett.* 69:433-435.

Mandelshtam et al. (1997) "Harmonic Inversion of Time Signals," *J. Chem. Phys.* 107(17):6756-6769.

Mandelshtam et al. (Sep. 8, 1998) Erratum "Harmonic Inversion of Time Signals and Its Applications," [*J. Chem. Phys.* 107:6756(1997)] *J. Chem. Phys* 109(10):4128.

Marie et al. (2002) "Adsorption Kinetics and Mechanical Properties of Thiol-Modified DNA-oligos on Gold Investigated by Microcantilever Sensors," *Ultramicroscopy* 91:29-36.

Martin et al. (2008) "Nanoscale Control of Exchange Bias with $BiFeO_3$ Thin Films," *Nano Lett.* 8(7):2050-2055.

Meier et al. (Aug. 2005) "Chemical Warfare Agent Detection Using MEMS-Compatible Microsensor Arrays," *IEEE Sens. J.* 5(4):712-725.

Melamud (2007) "Temperature-Compensated High-Stability Silicon Resonators," *Appl. Phys. Lett.* 90: 244107.

Najafi et al. (Oct. 1994) "A Micromachined Ultra-Thin-Film Gas Detector," *IEEE Trans. Electron. Dev.* 41(10):1770-1777.

Nelson et al. (2006) "Direct Deposition of Continuous Metal Nanostructures by Thermal Dip-Pen Nanolithography," *Appl. Phys. Lett.* 88(3):033104.

Nelson et al. (2007) "Measuring Material Softening with Nanoscale Spatial Resolution Using Heated Silicon Probes," *Rev. Sci. Instrum.* 78:023702.

Nelson et al. (2007) "Temperature Calibration of Heated Silicon Atomic Force Microscope Cantilevers," *Sens. Actuators A* 140:51-59.

Nelson, B.A. (May 2007) "Nanoscale Thermal Processing Using a Heated Atomic Force Microscope Tip," Ph.D. Dissertation, Georgia Institute of Technology.

Oden (1996) "Uncooled Thermal Imaging Using a Piezoresistive Microcantilever," *Appl. Phys. Lett.* 69(21): 3277-3279.

Olson et al. (Jun. 2003) "The Design and Operation of a MEMS Differential Scanning Nanocalorimeter for High-Speed Heat Capacity Measurements of Ultrathin Films," *J. Microelectromech. Syst.* 12(3):355-364.

Olson et al. (Feb. 1, 2005) "Size-Dependent Melting of Bi Nanoparticles," *J. AppL Phys.* 97:034304.

Pabst et al. (2007) "Leakage Mechanisms in $BiFeO_3$ Thin Films," *Appl. Phys. Lett.* 90:072902.

Pagonis et al. (2004) "Fabrication and Testing of an Integrated Thermal Flow Sensor Employing Thermal Isolation by a Porous Silicon Membrane Over an Air Cavity," *J. Micromech. Microeng.* 14:793-797.

Pantel et al. (2010) "Switching Kinetics in Epitaxial $BiFeO_3$ Thin Films," *Appl. Phys. Lett.* 107:084111.

Park et al. (2007) "Low Temperature Characterization of Heated Microcantilevers," *J. Appl. Phys.* 101:094504.

Park et al. (2007) "Topography Imaging with a Heated Atomic Force Microscope Cantilever in Tapping Mode," *Rev. Sci. Instrum.* 78(4):043709.

Park et al. (2008) "Routine Femtogram-Level Chemical Analyses Using Vibrational Spectroscopy and Self-Cleaning Scanning Probe Microscopy Tips," *Anal. Chem.* 80:3221-3228.

Park et al. (Apr. 2007) "Frequency-Dependent Electrical and Thermal Response of Heated Atomic Force Microscope Cantilevers," *J. Microelectromech. Syst.* 16(2):213-222.

Pedrak et al. (2003) "Micromachined Atomic Force Microscopy Sensor with Integrated Piezoresistive Sensor and Thermal Bimorph Actuator for High-Speed Tapping-Mode Atomic Force Microscopy Phase-Imaging in Higher Eigenmodes," *J. Vac. Sci. Technol. B* 21(6):3102-3107.

Pinnaduwage et al. (Nov. 2004) "A Sensitive, Handheld Vapor Sensor Based on Microcantilevers," *Rev. Sci. Instrum.* 75(11):4554-4557.

Pinnaduwage et al. (Oct. 2, 2003) "A Microsensor for Trinitoluene Vapour," *Nature* 425:474.

Pintilie et al. (2009) "Orientation-Dependent Potential Barriers in Case of Epitaxial $Pt$-$BiFeO_3$-$SrRuO_3$ Capacitors," *Appl. Phys. Lett.* 94:232902.

Pogorelov et al. (2010) "Corrected Field Enhancement Factor for the Floating Sphere Model of Carbon Nanotube Emitter," *J. Appl. Phys.* 108:044502.

Privorotskaya et al. (Web Release Apr. 8, 2009) "Silicon Microcantilever Hotplates with High Temperature Uniformity," *Sens. Act. A* 152:160-167.

Rabe et al. (1996) "Vibrations of Free and Surface-Coupled Atomic Force Microscope Cantilevers: Theory and Experiment," *Rev. Sci. Instrum.* 67(9):3281-3293.

Rabe et al. (2000) "Quantitative Determination of Contact Stiffness Using Atomic Force Acoustic Microscopy," *Ultrasonics* 38(1-8):430-437.

Rasmussen et al. (2003) "Optimized Cantilever Biosensor with Piezoresistive Read-Out," *Ultramicroscopy* 97:371-376.

Ravi et al. (Nov. Dec. 1991) "Oxidation Sharpening of Silicon Tips," *J. Vac. Sci. Technot B.* 9:2733-2737.

Reggiani et al. (2002) "Electron and Hole Mobility in Silicon at Large Operating Temperatures—Part I: Bulk Mobility," *IEEE Trans Electron Dev.* 49(3):490-499.

(56) References Cited

OTHER PUBLICATIONS

Remmert et al. (Oct. 2007) "Contact Potential Measurement Using a Heated Atomic Force Microscope Tip," *Appl. Phys. Lett.* 91(14):143111.

Remmert. (May 2007) "Nano Thermal and Contact Potential Analysis with Heated Probe Tips," M.S. Dissertation, Georgia Institute of Technology.

Riege (1994) "Electron Emission from Ferroelectrics—A Review," *Nuc. Instr. Meth. Phys. Res. A* 340:80-89.

Rinaldi et al. (2007) "Tuning the Dynamic Behavior of Cantilever MEMS Based Sensors and Actuators," *Sens. Rev.* 27(2):142-150.

Rinaldi et al. (2008) "Frequency Tuning AFM Optical Levers Using a Slot," *Microsyst. Technol.* 14(3):361-369.

Rosenblum et al. (1974) "Thermally Stimulated Field Emission from Pyroelectric $LiNbO_3$," *App. Phys. Lett.* 25:17-19.

Rosenman et al. (1984) "Electron Emission During the Switching of Ferroelectric Lead Germanate," *J. Exp. Theor. Phys. Lett.* 39:477-480.

Rosenmann et al. (Dec. 2000) "Electron Emission from Ferroelectrics," *J. Appl. Phys.* 88(11):6109-6161.

Roylance et al. (Dec. 1979) "A Batch-Fabricated Silicon Accelerometer," *IEEE Trans. Elec. Dev.* 26(12):1911-1917.

Rozenman et al. (Dec. 1980) "Exoelectron Emission Accompanying the Transverse Piezoelectric Effect in Lithium Niobate," *Sov. Tech. Phys. Lett.* 6(12):661-662; English translation of; *Pis'ma Zh. Tekh. Fiz.* 6, 1531 (1980).

Sadewasser (2006) "Special Cantilever Geometry for the Access of Higher Oscillation Modes in Atomic Force Microscopy," *Appl. Phys. Lett.* 89(3):3.

Sadewasser et al. (2006) "Modified Atomic Force Microscopy Cantilever Design to Facilitate Access of Higher Modes of Oscilllation," *Rev. Sci. Instrum.* 77:073703.

Sahin et al. (2004) "High-Resolution Imaging of Elastic Properties Using Harmonic Cantilevers," *Sens. Actuators A: Physical* 114(2-3):183-190.

Salmain et al. (1991) "Fourier Transform Infrared Spectroscopic Method for the Quantitative Trace Analysis of Transition-Metal Carbonyl-Labeled Bioligands," *Anal. Chem.* 63:2323-2329.

Sberveglieri et al. (Aug. 1997) "Silicon Hotplates for Metal Oxide Gas Sensor Elements," *Microsyst. Tech.* 3:183-190.

Seidel et al. (2009) "Conduction at Domain Walls in Oxide Multiferroics," *Nature Mat.* 8:229-234.

Semancik et al. (1998) "Kinetically Controlled Chemical Sensing Using Micromachined Structures," *Acc. Chem. Res.* 31:279-287.

Shannon et al. (1997) "Dual Mode Electron Emission from Ferroelectric Ceramics," *Appl. Phys. Lett.* 70:1625-1627.

Sharp et al. (1982) "Use of Low-Frequency Sinusoidal Temperature Waves to Separate Pyroelectric Currents from Nonpyroelectric Currents. Part II: Experiment," *J. Appl. Phys.* 53:8980-8987.

Sheehan et al. (Aug. 30, 2004) "Nanoscale Deposition of Solid Inks via Thermal Dip Pen Nanolithography," *Appl. Phys. Lett.* 85(9):1589-1591.

Sheng et al. (Jun. 25, 1998) "A Low-Power CMOS Compatible Integrated Gas Sensor Using Maskless Tin Oxide Sputtering," *Sens. Actuators B. Chem.* 49:81-87.

Shirke et al. (May-Jun. 2007) "Femtomolar Isothermal Desorption Using Microhotplate Sensors," *J. Vac. Sci. Technol. A* 25:514-526.

Shur et al. (1996) "Plasma-Assisted Electron Emission from $(Pb,La)(Zr,Ti)O_3$ Ceramic Cathodes," *J. Appl. Phys.* 79:3669-3674.

Shur et al. (1996) "Surface Discharge Plasma Induced by Spontaneous Polarization Switching," *Appl. Phys. Lett.* 70:574-576.

Shur et al. (1998) "A High-Perveance Ferroelectric Cathode with a Narrowed Electron Energy Spread," *J. Phys. D: Appl. Phys.* 31:1375-1382.

Shur et al. (1999) "Two Modes of Plasma-Assisted Electron Emission from Ferroelectric Ceramics," *J. Phys. D: Appl. Phys.* 32:L29-L33.

Solzbacher et al. (2003) "A Comprehensive Analytical and Numerical Analysis of Transient and Static Micro Hotplate Characteristics," In; *Transducers '03*, The 12th international Conference on Solid State Sensors, Actuators and Microsystems, Boston, : 1856-1859.

Solzbacher et al. (Jun. 10, 2000) "A Modular System of SiC-Based Microhotplates for the Application in Metal Oxide Gas Sensors," *Sens. Actuators B Chem.* 64:95-101.

Spannhake et al. (2007) "$SnO_2$: Sb—A New Material for High-Temperature MEMS Heater Applications: Performance and Limitations," *Sens Actuators B Chem.* 124:421-428.

Sprunt et al. (Sep. 1997) "Simultaneous FT-Raman Differential Scanning Calorimetry Measurements Using a Low-Cost Fiber-Optic Probe," *Appl. Spectrosc.* 51:1410-1414.

Stark (Nov. 2004) "Optical Lever Detection in Higher Eigenmode Dynamic Atomic Force Microscopy," *Rev. Sci. Instrum.* 75(11):5053-5055.

Stark et al. (May 31, 1999) "Tapping-Mode Atomic Force Microscopy and Phase-Imaging in Higher Eigenmodes," *Appl. Phys. Lett.* 74(22):3296-3298.

Su et al. (2002) "Characterization of a Highly Sensitive Ultra-Thin Piezoresistive Silicon Cantilever Probe and Its Application in Gas Flow Velocity Sensing," *J. Micromech. Microeng.* 12:780-785.

Suehle et al. (Mar. 1993) "Tin Oxide Gas Sensor Fabricated Using CMOS Micro-Hotplates and In situ Processing," *IEEE Electron Dev. Lett.* 14(3):118-120.

Sulchek et al. (May 2000) "High-Speed Atomic Force Microscopy in Liquid," *Rev. Sci. Instrum.* 71(5):2097-2099.

Sunden et al. (2006) "Room-Temperature Chemical Vapor Deposition and Mass Detection on a Heated Atomic Force Microscope Cantilever," *Appl. Phys. Lett.* 88:033107.

Szoszkiewicz et al. (2007) "High-Speed, Sub-15 nm Feature Size Thermochemical Nanolithography," *Nano Lett.* 7(4):1064-1069.

Thundat et al. (Feb. 1, 1995) "Vapor Detection Using Resonating Microcantilevers," *Anal. Chem.* 67(3): 519-521.

Thundat et al. (Mar. 27, 1995) "Detection of Mercury Vapor Using Resonating Microcantilevers," *Appl. Phys. Lett.* 66(13):1695-1697.

Thundat et al. (May 23, 1994) "Thermal and Ambient-Induced Deflections of Scanning Force Microscope Cantilevers," *Appl. Phys. Lett.* 64(21):2894-2896.

Tortonese et al. (Feb. 22, 1993) "Atomic Resolution with an Atomic Force Microscope Using Piezoresistive Detection," *Appl. Phys. Lett.* 62(8):834-836.

Triantafyllopoulou et al. (2006) "Alternative Micro-Hotplate Design for Low Power Sensor Arrays," *Microelectron. Eng.* 83:1189-1191.

Tsamis et al. (Oct. 15, 2003) "Thermal Properties of Suspended Porous Silicon Micro-Hotplates for Sensor Applications," *Sens. Actuators B Chem.* 95:78-82.

Udrea et al. (Aug. 30, 2001) "Design and Simulations of SOICMOS Micro-Hotplate Gas Sensor," *Sens. Actuators B Chem.* 78:180-190.

Unal et al. (2006) "Ultrafast Molecule Sorting and Delivery by Atomic Force Microscopy," *Appl. Phys. Lett.* 88: 183105.

Unal et al. (2007) "Nanoscale Quantitative Stress Mapping with Atomic Force Microscopy," *Appl. Phys. Lett.* 90: 113111.

Varesi et al. (1998) "Scanning Joule Expansion Microscopy at Nanometer Scales," *Appl. Phys. Lett.* 72(1):37-39.

Vettiger et al. (Mar. 2002) "The 'Millipede'—Nanotechnology Entering Data Storage," *IEEE Trans. Nanotechnol.* 1(1):39-55.

Vodopyanov et al. (2003) "Pulsed Mid-IR Optical Parametric Oscillators," In *Solid-State Mid-Infrared Laser Sources*; Sorokina et al. Eds. *Topics Appl. Phys.* 89:141-178.

Washburn et al. (2005) "Micro-Flame Ionization Detection Using a Catalytic Micro-Combustor," 2005 *IEEE Sensors* :322-325.

Wiche et al. (Sep. 23, 2005) "Thermal Analysis of Silicon Carbide Based Micro Hotplates for Metal Oxide Gas Sensors," *Sens. Actuators A. Phys.* 123-124:12-17.

Williams et al (1986) "Scanning Thermal Profiler," *Appl. Phys. Lett.* 49(23):1587-1589.

Wu et al. (Sep. 2001) "Bioassay of Prostate-Specific Antigen (PSA) using Microcantilevers," *Nat. Biotechnol.* 19:856-860.

Xiao et al. (2008) "Large Pyroelectric Effect in Undoped Epitaxial $Pb(Zr, Ti)O_3$ Thin Films on $SrTiO_3$ Substrates," *Appl. Phys. Lett.* 93:052913.

Yang et al. (2006) "Nano-Mechanical Electro-Thermal Probe Array Used for High-Density Storage Based on NEMS Technology," *Microelec. Reliability* 46:805-810.

(56) References Cited

OTHER PUBLICATIONS

Yang et al. (2010) Above-Bandgap Voltages from Ferroelectric Photovoltaic Devices, *Nature Nanotechnol.* 5:143-147.

Yu et al. (Jul. 19, 2010) "Interface Ferromagnetism and Orbital Reconstruction in $BiFeO_3$-$La_{0.7}Sr_{0.3}MnO_3$ Heterostructures," *Phys. Rev. Lett.* 105:027201.

Zeches et al. (Nov. 13, 2009) "A Straindriven Morphotropic Phase Boundary in $BiFeO_3$," *Science* 326(5955):977-980.

Zeyen et al. (2007) "Design and test of a novel higher harmonic imaging AFM probe with a dedicated second cantilever for harmonic amplification," Transducers and Eurosensors '07—14th International Conference on Solid-State Sensors, Actuators and Microsystems :1545-1548.

Zeyen et al. (2008) "Preamplifying cantilevers for contact resonance mode imaging," Solid-State Sensors, Actuators, and Microsystems Workshop, Hilton Head Island, South Carolina, Jun. 1-5, 44-47.

Zeyen et al. (2009) "Preamplifying Cantilevers for Dynamic Atomic Force Microscopy," *Appl. Phys. Lett.*, 94:103507.

Zhang et al. (Feb. 2011) "Large Field-Induced Strains in a Lead-Free Piezoelectric Material," *Nature Nanotechnol.* 6:98-102.

Zhang et al. (Aug. 2007) "Nanoscale Calorimetry Using a Suspended Bridge Configuration," *J. Microelectromech Syst.* 16(4):861-871.

Zhang et al. (Feb. 14, 2006) "A Micro-Pirani Vacuum Gauge Based on Micro-Hotplate Technology," *Sens. Actuators A Phys.* 126:300-305.

Zhang et al. (Jan. 17, 2005) "Thermal Characterization of Liquids and Polymer Thin Films Using a Microcalorimeter," *Appl. Phys. Lett.* 86(3):034101.

Zhang et al. (Oct. 15, 2000) "Size-Dependent Melting Point Depression of Nanostructures: Nanocalorimetric Measurements," *Phys. Rev. B. Condens Matter* 62(15):10548-10557.

Zhao et al, (2006) "Thermal Contributions to the Bending of Bimaterial Cantilever Sensors," *Appl. Phys. Lett.* 89:033110.

Zhong et al. (1993) "Fractured Polymer Silica Fiber Surface Studied by Tapping Mode Atomic-Force Microscopy," *Surf. Sci.* 290(1-2):L688-L692.

\* cited by examiner

| | |
|---|---|
| ▦ | Si Device Layer |
| ▨ | BOX |
| ▦ | Si Handle |
| ▩ | PR |
| ▩ | Metal (Al) |
| ■ | $Si_3N_4$ |
| ▩ | Doped Si |
| ■ | $Si_3N_4$ over Doped Si or Metal (Al) |

Figure 15

| Device type | Energy balance | Characteristics |
|---|---|---|
| A | $Q_{Gen} = Q_{Cond,Tethers} + Q_{Cond,Air,Top} + Q_{Cond,Air-Bottom}$ $$P = \frac{4\left(\sum_{i=1}^{n} k_i T_i\right) W}{L_T} \Delta\Theta + \frac{2\pi k_{Air}}{1/r_i - 1/r_{OT}} \Delta\Theta + \frac{2\pi k_{Air}}{1/r_i - 1/r_{OB}} \Delta\Theta$$ | • Suspended membrane released from the top side<br>• Sacrificial layer or high doped etch stop layer required<br>• Dominant air conduction through the air gap (g)<br>• Pirani gauge application<br>• $Q_{Cond,Air,Bottom}$ should be replaced with the rarefied gas conduction model when $g \ll L_H$. |
| B | $Q_{Gen} = Q_{Cond,Tethers} + Q_{Cond,Membrane} + Q_{Cond,Air}$ $$P = \frac{4\left(\sum_{i=1}^{n} k_i T_i\right) W}{L_T} \Delta\Theta + \frac{2\pi k_S T_M}{\ln(r_M/r_H)} \Delta\Theta + \frac{4\pi k_{Air}}{1/r_i - 1/r_O} \Delta\Theta$$ | • Suspended membrane released from the bottom side<br>• Bulk micromachining<br>• Dielectric membrane left intentionally<br>• Microfluidic components integration |
| C | $Q_{Gen} = Q_{Cond,Tethers} + Q_{Cond,Air}$ $$P = \frac{4\left(\sum_{i=1}^{n} k_i T_i\right) W}{L_T} \Delta\Theta + \frac{4\pi k_{Air}}{1/r_i - 1/r_O} \Delta\Theta$$ | • Suspended membrane released from the bottom side<br>• Bulk micromachining<br>• Dielectric membrane removed<br>• Best heating efficiency (thermal resistance)<br>• Worst response time |

US 8,931,950 B2

DEVICE FOR CALORIMETRIC MEASUREMENT

CROSS-REFERENCE TO RELATED APPLICATIONS

This application claims the benefit of and priority to U.S. Provisional Application 61/090,449, filed on Aug. 20, 2008, and PCT International Application PCT/US2009/054539, filed on Aug. 20, 2009, each of which is hereby incorporated by reference in its entirety.

STATEMENT REGARDING FEDERALLY SPONSORED RESEARCH OR DEVELOPMENT

This invention was made with United States governmental support under Award No. B568604 awarded by the United States Department of Energy. The United States government has certain rights in the invention.

BACKGROUND OF THE INVENTION

This invention is in the field of microcalorimetry. This invention relates generally to devices for performing calorimetry at small scales. In another aspect, the invention relates to methods of making calorimetric measurements.

A calorimeter is a widely used analytical instrument that measures heat release or absorption by a sample under test. The main components in calorimeters are heating and temperature sensing elements such that the sample under test can be heated and cooled in a temperature controlled manner. A differential scanning calorimeter (DSC) is one of the most routinely used calorimeters for characterizing metals or polymers, in which fast scanning in wide temperature ranges is possible while rejecting common-mode signals, thus enhancing sensitivity. Since DSC is a differential metrology, the reference and sample must be thermally decoupled. While both heaters are operated with a fixed temperature ramp, the differential power is measured and provides information regarding phase transition, temperature corresponding to and heat accompanied by a specific transition, such as a glass transition, crystallization, melting, or decomposition.

Microelectromechanical systems (MEMS) technologies have aided the development of microfabricated calorimeters, such as a DSC. Because of its small size, a microDSC consumes orders of magnitude smaller sample volumes, as well as offering fast operation and improved sensitivity. Since a microDSC can analyze sample quantities ranging from microgram to nanogram, for example, it offers the possibility to analyze costly or rare material samples, and can also be used to measure size-dependent thermodynamic properties.

Several different configurations have been offered for a MEMS-based DSC. In general, most microfabricated calorimeters previously reported have employed a dielectric structural membrane and a metal heater and thermometer. The thermal time constant of the previous designs are often limited by the low thermal conductivity of the dielectric membrane. Moreover, the metal heater and thermometer generally have long-term stability issues caused by electromigration. For example, a thin-film DSC (TDSC) consisting of a metal heater and thermometer on a thin dielectric film has been fabricated and used to measure size-dependent depression of melting point and reduction of enthalpy of fusion of thin metallic films and glass transition of thin polymeric films.

A suspended bridge small-scale DSC having a heater and temperature sensor isolated from and connected to a bulk chip via tethers was reported to achieve better temperature uniformity in the heater and a rectangular micro hotplate type microDSC has been employed for combustible gas sensing. Most previous works on micro differential scanning calorimetry focused on reducing thermal capacity of the device but in general there is a lack of detailed thermal design analysis and experimental validation regarding heating efficiency and response time.

International Application Publication No. WO 2006/073426 discloses a microcalorimeter comprising a semiconductor substrate having a thin membrane of a low heat capacity material (e.g., $Si_3N_4$ or SiC) deposited on a suspended plate and includes a gold or chromium heater and a thin film AuGe thermometer.

U.S. Patent Application Publication No. US 2004/0195096 discloses a calorimetric type gas sensor comprising a suspended porous silicon membrane having an insulating layer of $SiO_2$ and/or $Si_3N_4$. A doped polycrystal silicon or Pt/Ti conducting heater is formed on top of the insulating layer. A second insulating layer is formed thereon, followed by a catalytic (e.g., Pt or Pd) layer deposited on top of the second insulating layer.

International Application Publication No. WO 2007/026177 discloses a gas sensing semiconductor device fabricated from a silicon substrate including an insulating $SiO_2$ layer, doped single crystal silicon resistive heater, and source and drain CMOS circuitry. An inorganic (e.g., $SnO_2$) or organic (polymer or pthalocyanine) gas sensing region is separated from the heater by a second insulating layer.

U.S. Pat. No. 5,451,371 discloses a gas sensor comprising a pair of polysilicon plates each having a Pt heating resistor and Pt temperature sensing resistor. A silicon nitride passivation layer covers the Pt resistors and a catalytic layer (e.g., Pt, Pd) is deposited on one of the polysilicon plates.

U.S. Pat. No. 6,436,346 discloses a micro calorimetric sensor formed from silicon or silicon dioxide having a platform with a resistive Platinum thermal detector thereon. A chemical coating is formed on the platform for operation of the sensor, and temperature control of the platform is achieved by adding a polysilicon heating resistor to the platform or a Peltier stage to the entire sensor.

SUMMARY OF THE INVENTION

To overcome the limitations of previous designs, a single crystal silicon microfabricated calorimeter is provided herein. Silicon has high thermal conductivity, comparable to that of metal, while exhibiting a heat capacity similar to commonly used dielectric materials (silicon dioxide and silicon nitride), thus improving the thermal time constant of the calorimeter. High thermal conductivity also offers better temperature homogeneity within the heater, and thus facilitates improved instrumentation and analysis.

In one aspect, provided herein is a single crystal silicon microcalorimeter, for example useful for high temperature operation and long-term stability of calorimetric measurements. Microcalorimeters described herein include microcalorimeter embodiments having a suspended structure and comprising single crystal silicon. Also provided herein are methods for making calorimetric measurements, for example, on small quantities of materials (e.g., µg or ng) or for determining the energy content of a material having an unknown composition.

In one embodiment, a microcalorimeter comprises a single crystal silicon suspended structure having a heater-thermometer, wherein the heater-thermometer comprises a region of doped single crystal silicon within the single crystal silicon suspended structure. For some embodiments, the suspended structure consists of or consists essentially of single crystal silicon and/or doped single crystal silicon; for other embodiments, the suspended structure comprises single crystal silicon and/or doped single crystal silicon. In some embodiments, the single crystal silicon suspended structure and heater-thermometer comprise a unitary structure and/or a single layer. In specific embodiments, the single crystal silicon suspended structure is a suspended platform and/or has a planar surface and/or has the heater-thermometer embedded therein.

Heater-thermometers useful with some embodiments include a heater-thermometer having a dopant concentration selected from $10^{19}$ to $10^{22}$ dopants/cm$^3$. In a specific embodiment, the heater-thermometer has a dopant concentration selected from $10^{20}$ to $10^{21}$ dopants/cm$^3$. Useful dopants include, but are not limited to, dopants selected from the group consisting of phosphorus, nitrogen, arsenic and antimony.

In a specific embodiment, a heater-thermometer has a resistance that is a function of temperature, allowing for a precise temperature of the heater-thermometer to be determined, for example, by a measurement of the resistance of the heater-thermometer. In other embodiments, the resistance of the heater-thermometer is fixed. Heater-thermometers useful with the microcalorimeters described herein include heater-thermometers having a resistance selected from the range of 0.1 to 100 kΩ and/or a resistance selected from the range of 1 to 10 kΩ.

In an embodiment, a heater-thermometer is useful for controlling the temperature of the single crystal silicon suspended structure, measuring the temperature of the single crystal silicon suspended structure, or both. In a specific embodiment, the heater-thermometer has a shape useful for providing a uniform temperature profile to the microcalorimeter. For example, the heater-thermometer may comprise a serpentine path across the single crystal silicon platform and/or have a width selected from the range of 0 to 20 μm, for example 5 μm.

The microcalorimeters described herein include embodiments having any shape useful for making calorimetric measurements. Example embodiments include those where the single crystal silicon suspended structure has a shape selected from the group consisting of square, rectangular, circular and polygon. In specific embodiments, the single crystal silicon suspended structure has a width selected from the range of 10 to 500 μm, and/or a thickness selected from the range of 0.05 to 5.0 μm. For example, the single crystal silicon suspended structure can have a width selected from the range of 90 to 100 μm and/or a thickness of 0.1 μm.

In some embodiments, a microcalorimeter further comprises one or more single crystal silicon tethers. For example, the microcalorimeter may comprise four single crystal silicon tethers positioned at the corners of a square or rectangular single crystal silicon suspended structure. In a specific embodiment, at least one single crystal silicon tether comprises doped single crystal silicon, for example having a dopant concentration selected from the range of $10^{19}$ to $10^{22}$ dopants/cm$^3$ or a dopant concentration selected from the range of $10^{20}$ to $10^{21}$ dopants/cm$^3$. Useful single crystal silicon tethers include tethers having a width selected from the range of 1 to 50 μm and/or a length selected from the range of 10 to 500 μm and/or a thickness selected from the range of 0.05 to 5.0 μm, for example tethers having a width of 10 μm, a length of 222 μm and a thickness selected from the range of 0.1 to 3.0 μm. In some embodiments, all the single crystal silicon tethers have the same dimensions; in other embodiments, the single crystal silicon tethers include a range of tether dimensions.

In specific embodiments, a microcalorimeter further comprises a resistance measuring circuit for measuring a resistance of the heater-thermometer and/or a current source for providing a current to the heater-thermometer. Useful resistance measuring circuits include any resistance measuring circuits known to the art, for example a Wheatstone bridge circuit.

In another aspect, provided herein are methods of making calorimetric measurements. The microcalorimeters described above are generally useful with the methods of this aspect. A specific method of this aspect comprises providing a microcalorimeter comprising a single crystal silicon suspended structure having a heater-thermometer and monitoring the temperature of the heater-thermometer. For example, the heater-thermometer can comprise a region of doped single crystal silicon within the single crystal silicon suspended structure. Some methods may also comprise the further step of providing a current to the heater-thermometer to raise the temperature of the heater thermometer.

When calorimetric measurements are to be performed on a specific compound, a method of this aspect further comprises the step of providing a compound to the surface of the suspended structure. In a specific embodiment, a method of determining the energy density of a combustible material comprises the steps of providing a microcalorimeter comprising a single crystal silicon suspended structure having a heater-thermometer, providing a combustible material to the surface of the suspended structure, providing a current to the heater-thermometer to raise the temperature of the heater-thermometer and the combustible material to initiate combustion of the combustible material, and monitoring the temperature of the heater-thermometer.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 15 illustrates a lumped heat transfer model and characteristics of three micro hotplate types.

FIG. 14

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

"Suspended structure" refers to a structure which is attached to one or more supports such that the structure is suspended over an opening or recessed region. A suspended structure may also refer to a structure which is held in place over an opening or a recessed region by one or more supports such that the structure partially covers the opening or recessed region. A suspended platform as used herein refers to a suspended structure having a planar or substantially planar surface, such a surface having an average divergence from planarity of less than 1 µm. For some embodiments, a suspended platform is a thin planar suspended structure, e.g. having an average thickness of 0.05 to 5.0 µm.

"Unitary structure" refers to a structure having one or more components within a single continuous or monolithic body, and includes structures having a uniform or non-uniform composition. For example, a block of single crystal silicon having a region of implanted dopants has a unitary structure.

"Tether" refers to a support member for holding a structure in place. For some embodiments, a tether refers to a support member which is longer than it is wide.

"Single crystal silicon" refers to a type of silicon structure composed of a single continuous silicon crystal. Single crystal silicon generally refers to a silicon crystal in which the silicon crystal lattice is continuous, however, single crystal silicon as referred to herein can include a single crystal silicon structure in which there are defects, interstitials, or dopants (e.g., doped, implanted or extrinsic single crystal silicon).

"Polycrystal silicon" refers to a type of silicon structure composed of many small silicon crystals of varying or random orientation. Unlike single crystal silicon, in polycrystal silicon there is generally no single continuous crystal lattice but rather many crystallites conglomerated into a larger structure.

Described herein is a micro calorimeter comprising single crystal silicon and useful at high temperatures, for example at temperatures above the melting point of many metals. The single crystal silicon micro calorimeters described herein exhibit superior thermal properties, allowing their use for sensitive calorimetric measurements, for example calorimetric measurements at the micro- or nano-scale (e.g., ng sample sizes, or structures having µm dimensions). The micro calorimeters described herein further include a doped heater-thermometer region. Such a doped heater-thermometer region is useful, for example, to allow a single crystal silicon microcalorimeter to have a planar surface.

Figure 1:
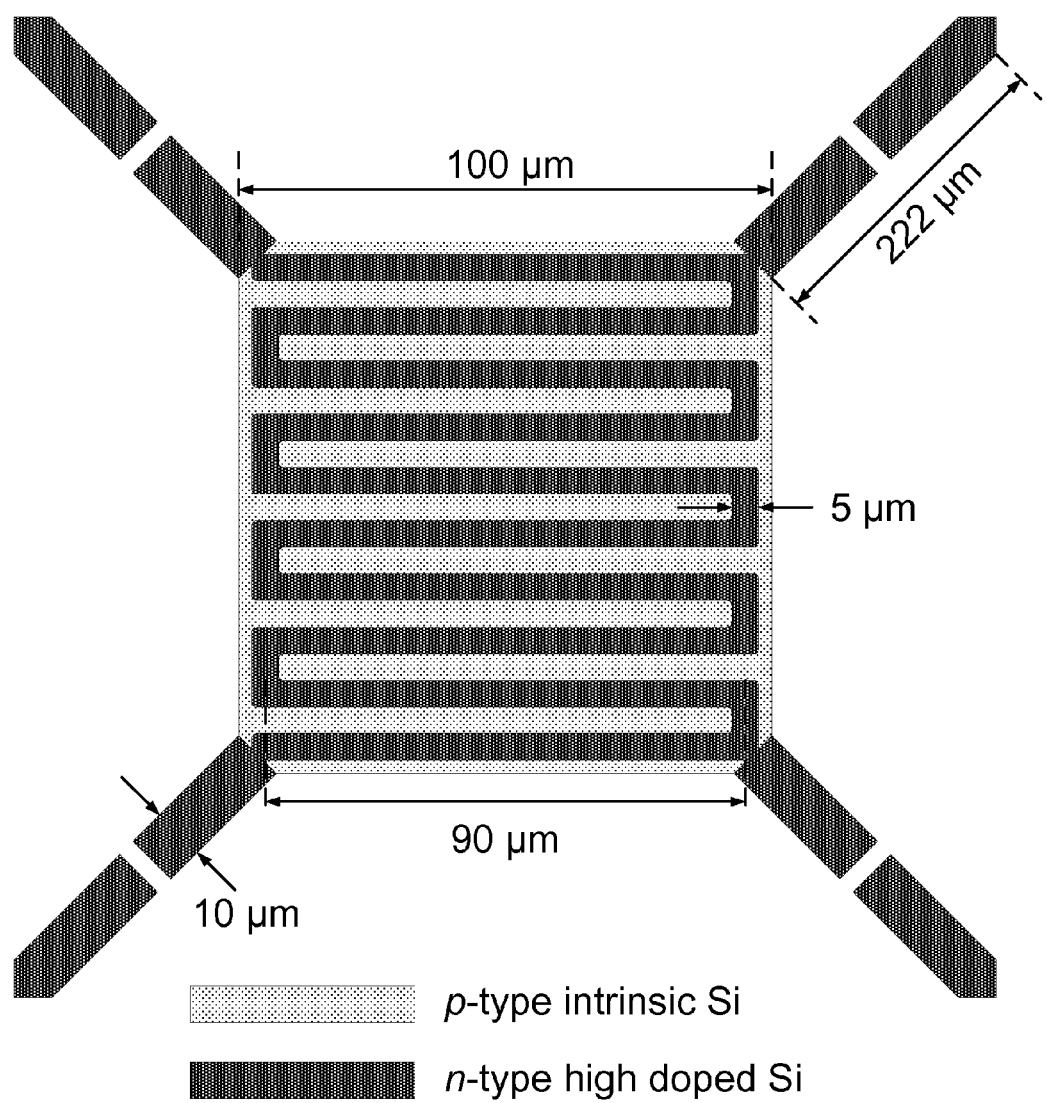
FIG. 1 illustrates the design of a micro calorimeter embodiment.
Figure 4:
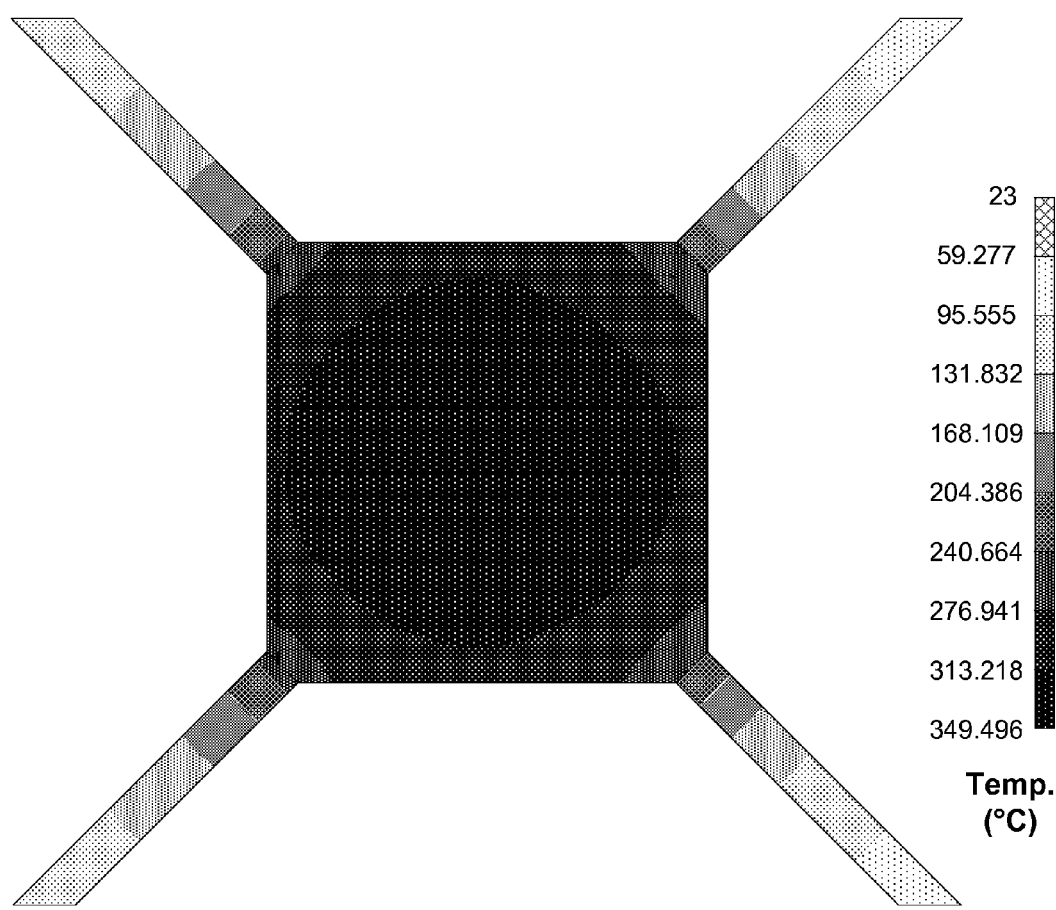
FIG. 4 shows a predicted temperature profile of the calorimeter of FIG. 1 when a DC bias of 9.27 V is applied across the heater-thermometer.

FIG. 1 illustrates a first micro calorimeter embodiment design. In this embodiment, the micro calorimeter has a p-type single crystal silicon suspended platform having a square shape with a 100 µm length/width dimension. A heater-thermometer region of n-type high-doped silicon follows a serpentine path over the platform and has a width of 5 µm. The heater-thermometer region is connected to four silicon tethers positioned at the corners of the square platform, where each tether has a width of 10 µm and a length of 222 µm. In some embodiments, the micro calorimeter further comprises a current supply electrically connected to the heater-thermometer region for providing a heating current to the microcalorimeter. For example the left pair of tethers in the micro calorimeter of FIG. 1 can be connected to a current supply. The heater-thermometer region of this micro calorimeter provides both heating and temperature sensing in a single element. In some embodiments, the micro calorimeter further comprises a resistance measuring circuit electrically connected to the heater-thermometer region for measuring a resistance of the heater-thermometer region. As the resistance across the heater-thermometer is temperature dependent, the temperature of the calorimeter of FIG. 1 can be monitored, for example, by connecting the right pair of tethers to a resistance measuring circuit. FIG. 4 shows a predicted temperature profile of the calorimeter of FIG. 1 when a DC bias of 9.27 V is applied across the heater-thermometer.

Figure 2:
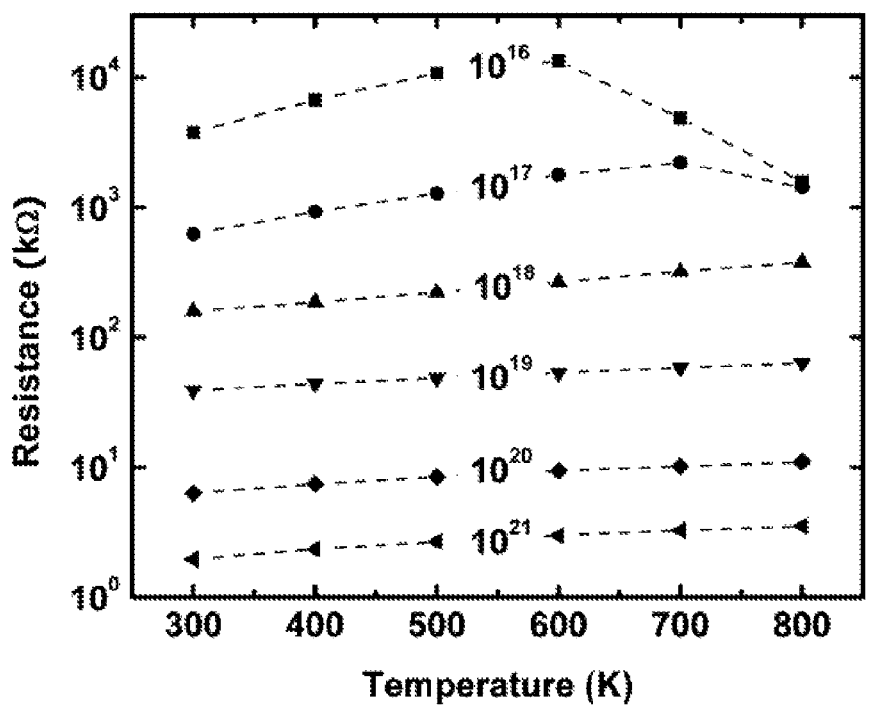
FIG. 2 illustrates an example heater-thermometer resistance as a function of temperature for a range of heater-thermometer dopant concentrations.
Figure 3:
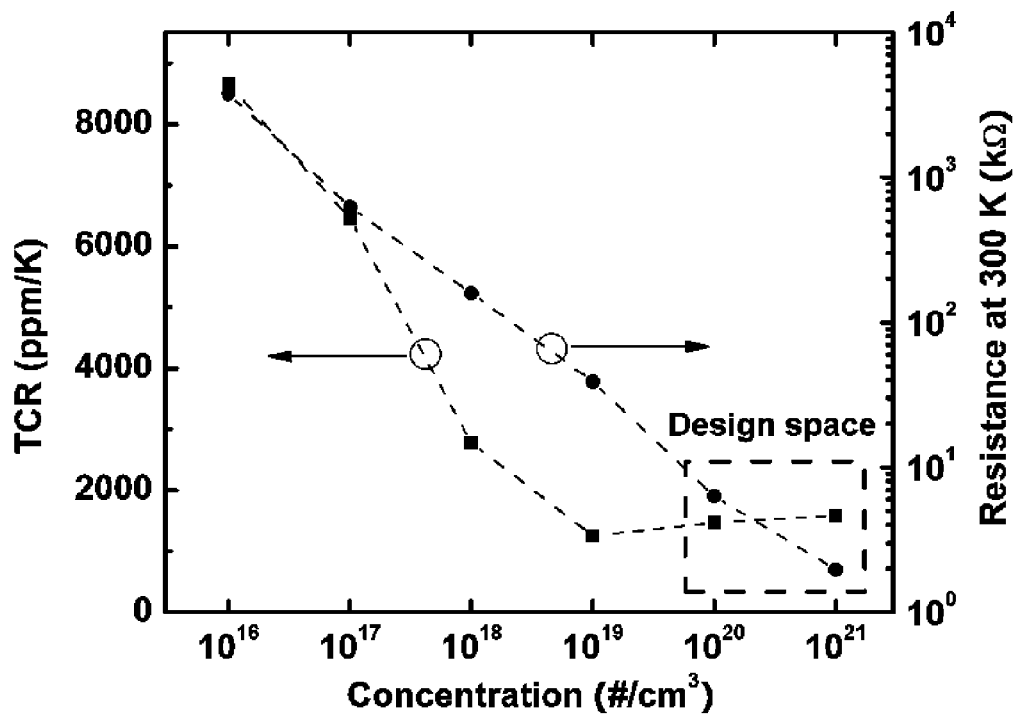
FIG. 3 illustrates the temperature coefficient of electrical resistance and heater-thermometer resistance at 300 K as a function of dopant concentration for an example micro calorimeter.

FIG. 2 illustrates an example heater-thermometer resistance as a function of temperature for a range of heater-thermometer dopant concentrations. FIG. 3 illustrates the temperature coefficient of electrical resistance and heater-thermometer resistance at 300 K as a function of dopant concentration for an example micro calorimeter.

Figure 5:
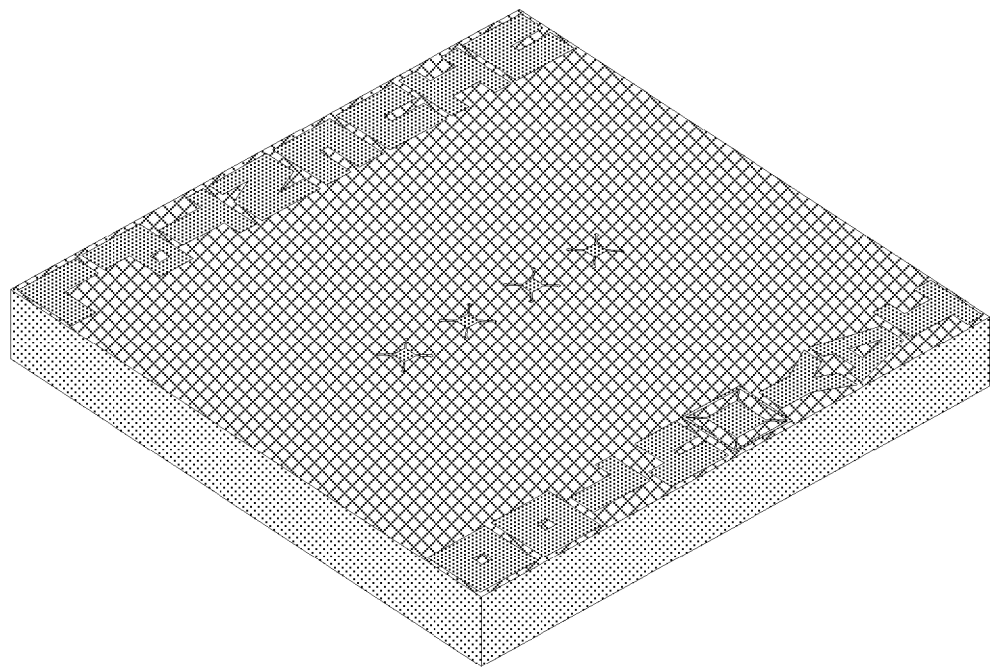
FIG. 5 shows the first major fabrication step for making a silicon microcalorimeter; the tethered membrane structures are etched into the device layer.
Figure 6:
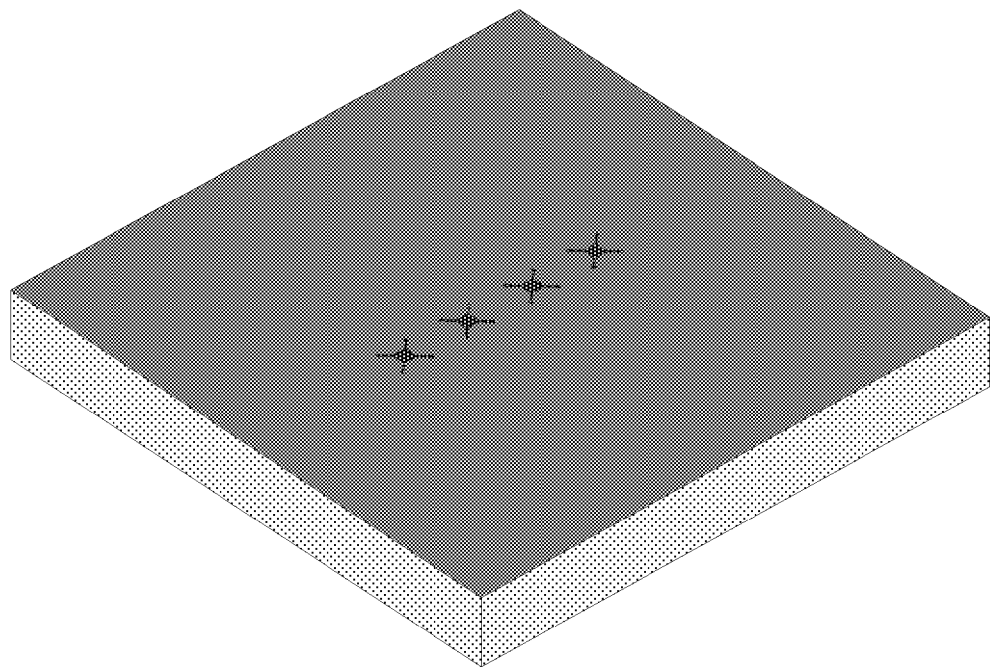
FIG. 6 shows the second major fabrication step for making a silicon microcalorimeter; serpentine heater and tethers are doped by implantation and post-diffusion.
Figure 7:
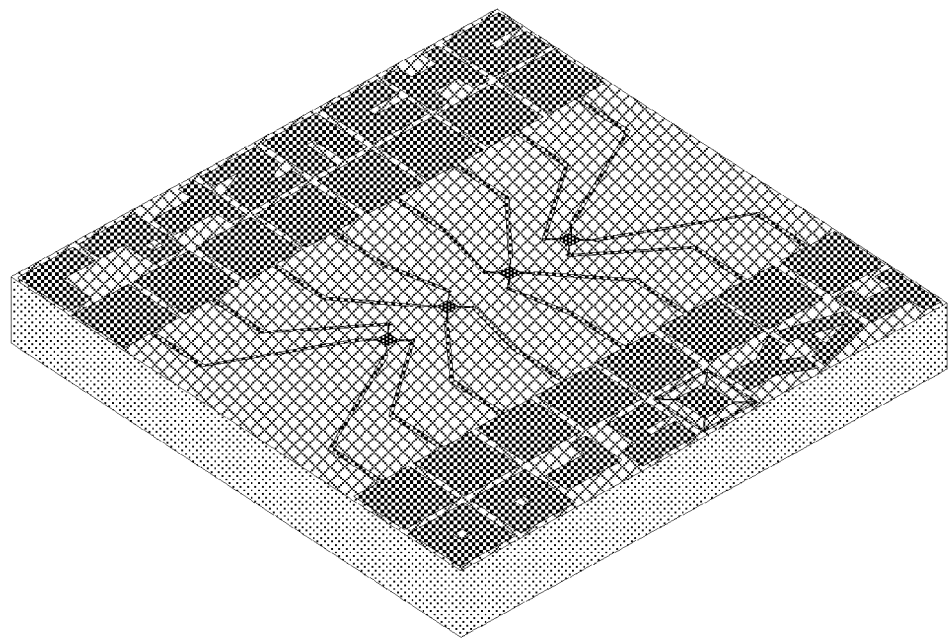
FIG. 7 shows the third major fabrication step for making a silicon microcalorimeter; Aluminum metallization is done using an electron beam evaporator and lift-off process.
Figure 8:
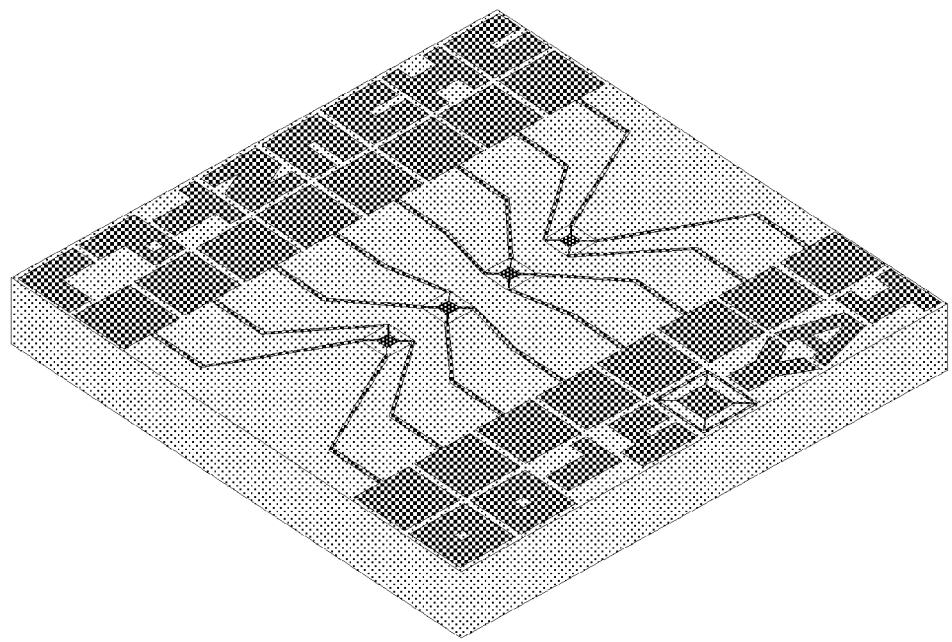
FIG. 8 shows the fourth major fabrication step for making a silicon microcalorimeter; the backside of the wafer is etched using ICP.
Figures 9, 10:
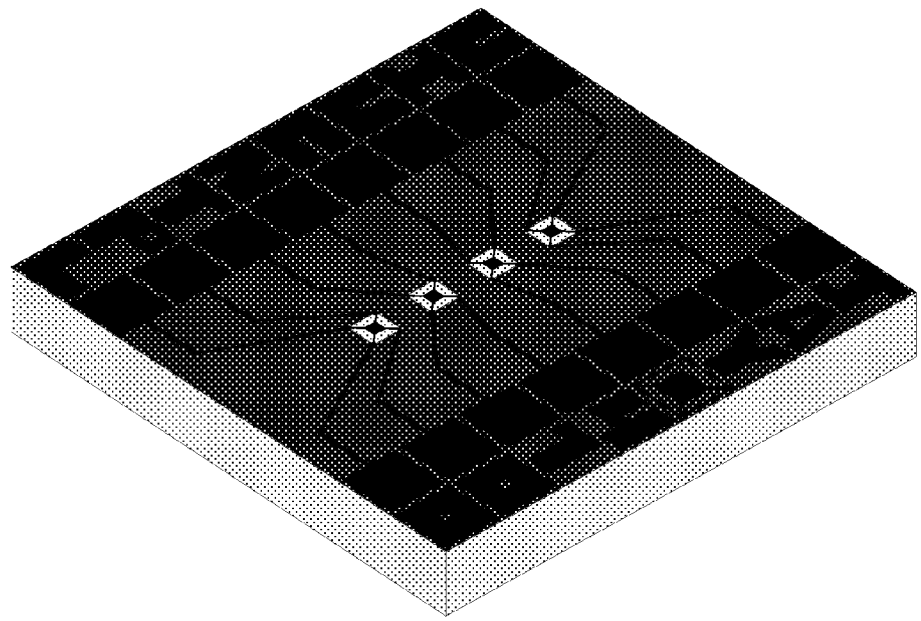
FIG. 9 shows the last major fabrication step for making a silicon microcalorimeter; PECVD nitride is added on the front side for passivation.
FIG. 10 provides a legend for FIGS. 5-9.

In one embodiment, FIGS. 5-10 show five major fabrication steps to make a silicon microcalorimeter. The fabrication process starts with a p-type silicon-on-insulator wafer (SOI-TEC) of orientation <100>. The tethered membrane structures are patterned first with a positive photoresist and etched into the silicon device layer using a Bosch process in an inductively coupled plasma (ICP) etcher (FIG. 5). Then, an implantation step is performed with hard-baked positive photoresist as a mask for ion implantation (FIG. 6). Exposed serpentine heater and tethers are doped, for example with phosphorous, nitrogen, arsenic or antimony. After selective implantation to define the heater, the photoresist implantation mask is removed, for example with acetone and hot Piranha solution. A silicon dioxide layer is then deposited on the entire wafer using plasma enhanced chemical vapor deposition (PECVD) to prevent dopants from diffusing back to the ambient during the subsequent heat treatment to anneal the damaged surface and further drive-in the dopants. After the heat treatment, the PECVD oxide is removed in buffered oxide etch (BOE) to expose the doped silicon for metallization. Electron beam evaporation in conjunction with a lift-off process can be used to define aluminum-doped silicon contacts (FIG. 7), followed by a sintering step to allow inter-diffusion of doped silicon and aluminum. Then, the backside of the wafer is patterned with a negative photoresist and etched using ICP until the buried oxide layer is exposed (FIG. 8). The microcalorimeters are finally released by immersion in hydrofluoric acid and PECVD nitride is deposited on the front side for passivation (FIG. 9). FIG. 10 shows the legend for FIGS. 5-9.

FIGS. 11a and 11b show scanning electron micrographs of a fabricated micro calorimeter. Four microcalorimeters are depicted which, each having a single crystal silicon suspended platform and independent electrical connections to four single crystal silicon tethers attached to each platform.

EXAMPLE 1

Design, Fabrication and Characterization of a Silicon Microfabricated Calorimeter Design.

In general, a silicon micro calorimeter shows better long-term stability than dielectric-metal calorimeters. FIG. 1 shows the design of a microfabricated calorimeter. A squared membrane exists at the center linked to the bulk silicon chip with four tethers. The length and width of the square membrane are each 100 µm and each tether is 10 µm wide and 222 µm long. Two tethers on the left are for heating and two tethers on the right for sensing. A serpentine heater track runs from a tether to another one through the island that will serve as a heater platform. Since only implanted and diffused resistors are employed, this design prevents any surface topology and achieves a planar surface. Doped silicon resistors have appreciable temperature coefficient of the resistance (TCR) compared to that of metals. Low-doped silicon can exhibit higher TCR than metal but its high resistance compromises signal to noise ratio (SNR). In contrast, high-doped silicon can offer better SNR while sacrificing TCR. Thus, there are trade-offs between room temperature resistance and TCR when selecting doping concentration. To this end, doping concentration dependent device resistance and TCR were investigated by employing a carrier mobility model. FIG. 2 shows heater resistance as a function of device temperature at different doping concentrations and FIG. 3 shows temperature coefficient of electrical resistance and heater resistance at 300 K as a function of doping concentration on left and right y-axis, respectively. These results allow for selection of optimal doping concentration for fabrication.

Based on geometry and electrical properties determined, finite element analysis (FEA) was performed to predict temperature dependent electrical properties and electrothermally induced heating. FIG. 4 shows FEA results where the average and standard deviation of the temperature of the effective heater (93 µm×93 µm) are 299.4° C. and 31.1° C., respectively. Required DC bias is 9.27 V.

Fabrication.

FIGS. 5-10 show the five major fabrication steps to make the silicon microcalorimeter. The fabrication process started with a p-type silicon-on-insulator wafer (SOITEC) of orientation <100>, where the silicon device layer was 340 nm, the buried oxide (BOX) layer was 400 nm, and the silicon handle layer was 450 µm. Resistivity in the device layer was 14~22 Ω-cm. The tethered membrane structures were patterned first with a positive photoresist (Shipley, 1827) and etched into the silicon device layer using a Bosch process in an inductively coupled plasma (ICP) etcher. Then, an implantation step was performed with hard-baked positive photoresist (Shipley, 1827) as a mask for ion implantation. Exposed serpentine heater and tethers were doped with $2.51 \times 10^{16}$ cm$^{-2}$ of phosphorous at 180 keV. After selective implantation to define the heater, the photoresist implantation mask was removed with acetone and hot (120° C.) Piranha (70% $H_2SO_4$:30% $H_2O_2$ in volume ratio) solution. A 200 nm thick silicon dioxide layer was deposited on the entire wafer using plasma enhanced chemical vapor deposition (PECVD) to prevent dopants from diffusing back to the ambient during the subsequent heat treatment to anneal the damaged surface and further drive-in the dopants. The heat treatment was performed in a furnace tube for 50 min at 1000° C. and distributed dopants into the device layer. After the heat treatment, the PECVD oxide was removed in buffered oxide etch (BOE) to expose the doped silicon for metallization. Electron beam evaporation in conjunction with a lift-off process defined aluminum-doped silicon contacts, a 30-minute sintering step at 400° C. was performed to allow inter-diffusion of doped silicon and aluminum. Then, the backside of the wafer was patterned with a thick negative photoresist (Futurrex, NR5-8000) and etched using ICP until the buried oxide layer was exposed. The microcalorimeters were finally released by a 30 sec. immersion in 49% hydrofluoric acid and PECVD nitride was deposited on the front side for passivation. FIGS. 11a and 11b show scanning electron micrographs of a fabricated micro calorimeter. Four calorimeters in a unit device exhibit identical electrical and thermal behaviors such that any two of them can be operated in a differential configuration.

Characterization.

Figure 12:
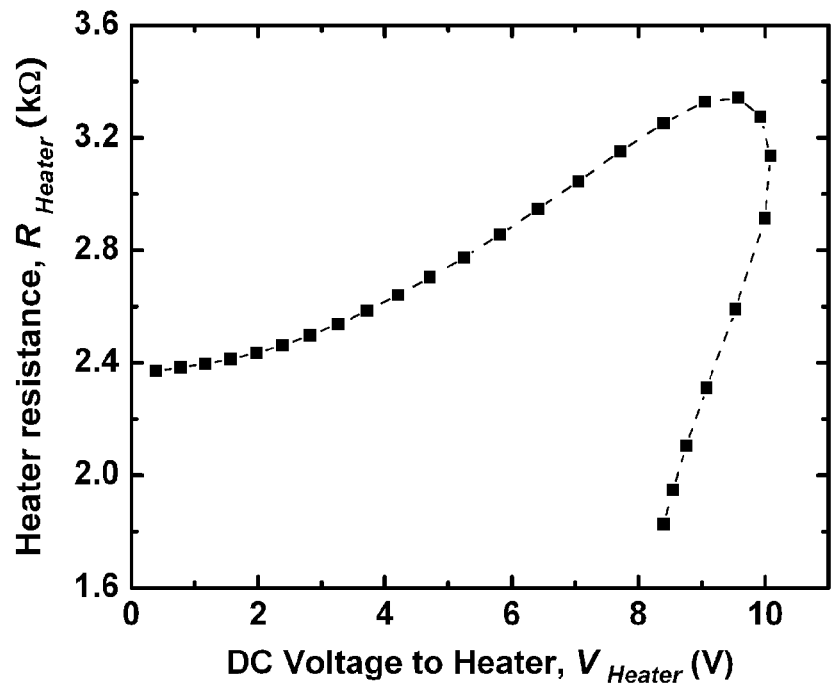
FIG. 12 illustrates data showing the electrical characterization of a fabricated microcalorimeter.
Figure 13:
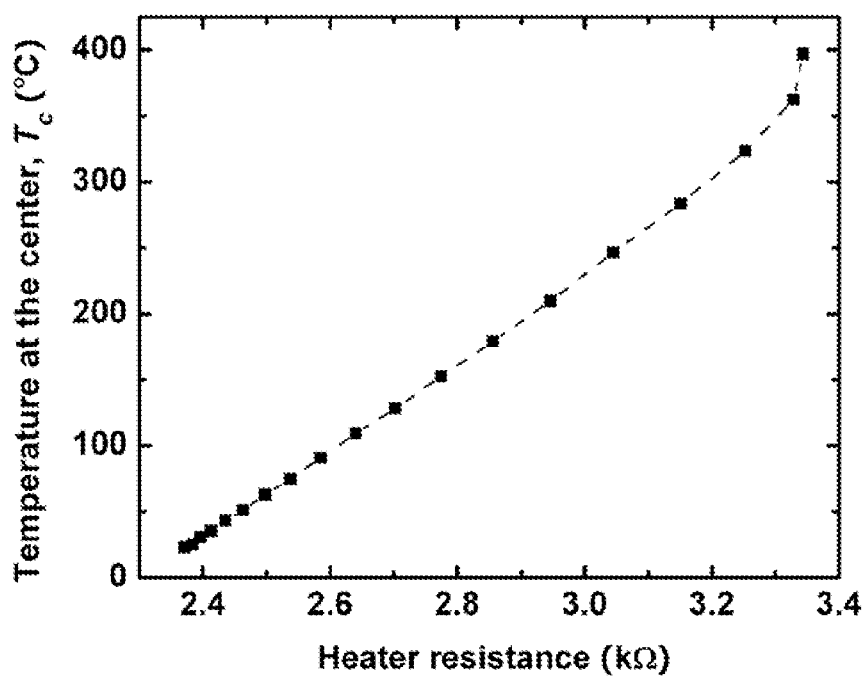
FIG. 13 illustrates Raman spectroscopy temperature calibration data.

After device fabrication, electrical and thermal characterization was performed and the results are shown in FIGS. 12 and 13. Heater resistance shows typical "thermal runaway" behavior of silicon MEMS devices where the TCR of the device undergoes from positive to negative. However, this does not limit temperature range of operation. By interfacing a current limiting resistor, the silicon microfabricated calorimeter can be heated to higher temperatures. Then, temperature at the center of the heater (TC) was measured using a laser Raman spectroscopy while the calorimeter was Joule-heated. FIG. 13 shows measured TC as a function of electrical resistance of the heater. The temperature coefficient of the resistance of the heater was calculated to be $1.223 \times 10^{-3}$ K$^{-1}$.

Using this temperature calibration, the temperature of the microfabricated calorimeter can be monitored from the heater resistance.

FIGURE DESCRIPTIONS

FIG. 1. Design of the microfabricated calorimeter. A squared island exists at the center linked to the bulk silicon chip with four tethers. A serpentine heater track runs from a tether to another one through the island that will serve as a heater platform. Two tethers on the left are for heating and two tethers on the right for sensing.

FIG. 2. Heater resistance as a function of temperature with different doping concentration.

FIG. 3. Temperature coefficient of electrical resistance (left y-axis) and heater resistance at 300 K (right y-axis) as a function of doping concentration.

FIG. 4. FEA results show the average and standard deviation of the temperature of the effective heater (93 μm×93 μm at center) are 299.4° C. and 31.1° C., respectively, where required DC bias is 9.27 V. Temperature unit in color bars is degree Celsius.

FIG. 5. First step: The tethered membrane structures are etched into the device layer.

FIG. 6. Second step: Serpentine heater and tethers are phosphorous doped by implantation and post-diffusion.

FIG. 7. Third step: Aluminum metallization is done using electron beam evaporator and lift-off process.

FIG. 8. Fourth step: The backside of the wafer is etched using ICP and then the buried oxide layer is etched in HF.

FIG. 9. Fifth step: PECVD nitride is added on the front side for passivation.

FIG. 10. Color bars indicate materials used in fabrication processes.

FIG. 11a. Scanning electron micrographs of the fabricated microcalorimeter. A differential scanning calorimeter (DSC) unit die having four identical devices, such that any two can offer differential measurements.

FIG. 11b. A close up of one device.

FIG. 12. Electrical characterization of the fabricated microcalorimeter.

FIG. 13. Temperature calibration is performed using micro Raman spectroscopy. The temperature coefficient of the resistance of the heater is calculated to be $1.223 \times 10^{-3}$ $K^{-1}$.

EXAMPLE 2

Differential Scanning Calorimeter Based on Suspended Membrane Single Crystal Silicon Micro Hotplate This example describes an array of single crystal silicon micro hotplates for differential scanning calorimetry (DSC). Heat transfer analysis considers the tradeoffs between heating and cooling rate, temperature uniformity, and measurement sensitivity, and determines the optimal design to be a suspended membrane micro hotplate with full backside release. Additionally considering the requirements of routine sample loading, the size of the square heater (LH) was chosen as 100 μm or 200 μm while the size of the suspended membrane was chosen as 400 μm. In the square heater region, two interdigitated serpentine doped silicon resistors were designed such that several operational configurations were possible. The hotplates exhibited very high heating efficiency of 36.7 K/mW with LH=100 μm and 18.3 K/mW with LH=200 μm while also having time constants on the order of 1 ms. Paraffin wax was mounted on fully calibrated micro hotplates for DSC. Paraffin melting transition was observed when the heater temperature was 55° C. with a slow linear voltage ramp of 0.2 V/s. With 8 V/s, loaded paraffin sample was completed consumed within 1 ms and associated thermal energy of 0.317 mJ was extracted. The micro hotplate DSC made of single crystal silicon achieves high temperature uniformity in the heater platform while offering a combination of time constant, temperature sensitivity, and heating efficiency that are comparable to or superior to previously published microcalorimeters.

Micro hotplates are MEMS devices designed for rapid heating, which typically consist of a closed or suspended membrane having embedded heaters and thermometers. Micro hotplates are predominantly used for gas sensing with metal oxide semiconductors changing their conductance with respect to specific gases. They can be used in virtually any application that requires rapid, small-scale heating and temperature sensing for applications such as micro solid oxide fuel cells, Pirani gauge, and DSC. Additionally, micro hotplates can be used to detect chemical warfare agents, measure femtomolar isothermal desorption in conjunction with mass spectroscopy, and detect micro flame ionization. The micro hotplate architecture, in which the heater is suspended by thin tethers, offers high heating efficiency for improved microDSC.

Despite numerous applications and practical usages of micro hotplates, the published literature regarding their thermal modeling and heat transfer analysis is inconsistent. Heat loss from a micro hotplate to the ambient air was attributed to either conduction or convection. The Grashof number, which is the ratio of measure of buoyancy forces to viscous forces, is typically in the range of 0.01 to 0.1 for these devices, and thus it is unlikely that natural convection plays a significant role in heat transfer near the micro hotplate. Nevertheless, some articles employed convection heat transfer coefficients of the order of 100 $W/m^2$ without experimental validation. Furthermore, both conduction and convection loss to the ambient air are included separately in some analyses, although in reality the diffusive and convective transport are not independent. Previously published literature mostly focused on a specific type of hotplate and could not provide more generalized design guidelines for micro hotplate applications.

A. Design Overview.

Figure 14:
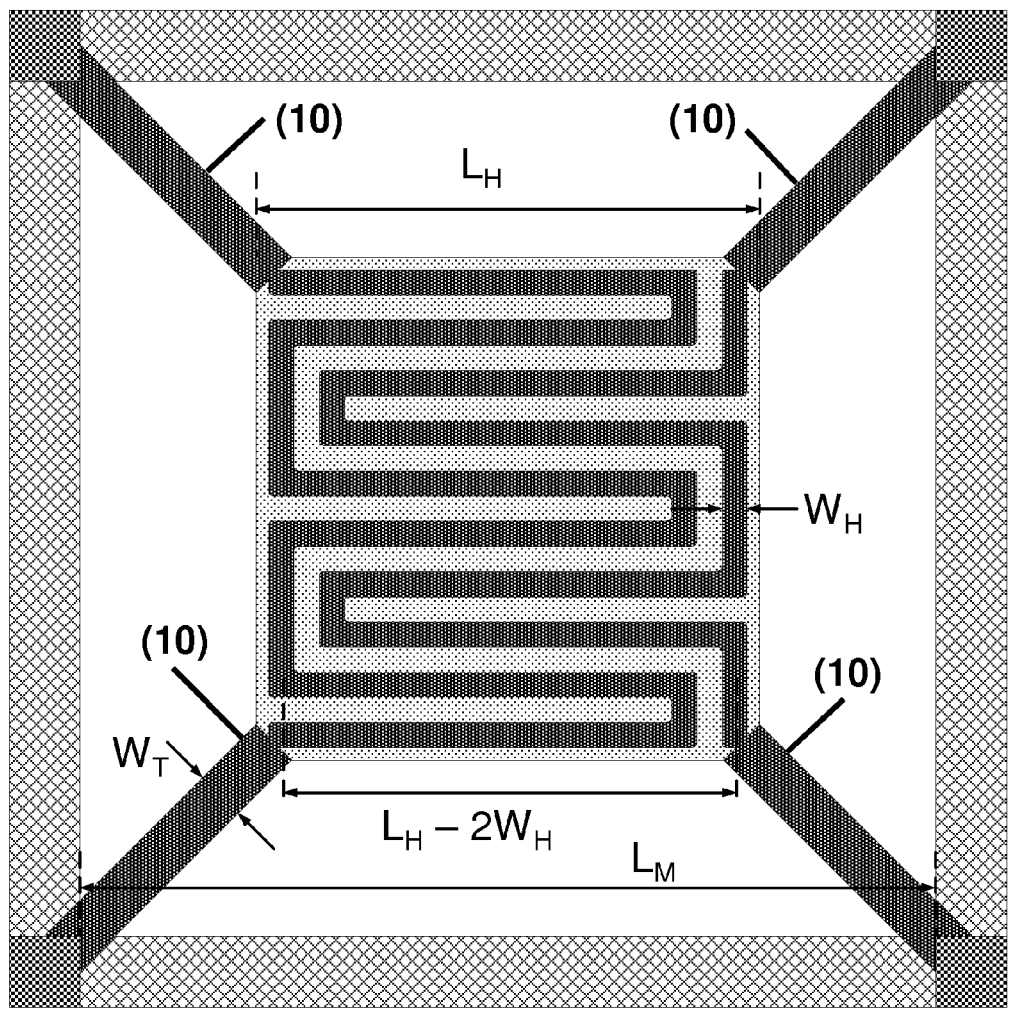
FIG. 14 shows the design of a second microfabricated calorimeter embodiment.

This example describes a micro hotplate, comprising a heater-thermometer element that is freely suspended via solid tethers, to construct a micro differential scanning calorimeter. FIG. 14 shows the design of the silicon micro hotplate calorimeter. A square island at the center is linked to the bulk silicon with four tethers (10). In the squared island, two interdigitated serpentine doped silicon resistors are implanted. Since only implanted and diffused resistors are employed, this design achieves a very smooth surface, which facilitates simultaneous operation of the micro hotplate with optical microscopes and vibrational spectroscopes. Two doped silicon resistors enable several operational configurations. For example, resistor L is used as a heater and resistor R is used as a resistive thermometer or both resistors can be used as heaters. In any possible configuration, the squared island will be designated as a heater. The heater with tethers can sit on a dielectric membrane (closed membrane) or be fully suspended (suspended membrane). Whereas closed membrane micro hotplates are usually released from the bottom, suspended membrane micro hotplates can be released from either the top or the bottom. Therefore, three possible device types can exist: Type A is the suspended membrane micro hotplate released from the top; type B is the closed membrane micro hotplate; and type C is the suspended membrane released from the bottom.

B. Heat Transfer Model.

Heat transfer from different micro hotplates to surroundings can be simply understood using lumped capacitance analysis. For conventional operation in air, thermal radiation and convection can be neglected considering the size of micro hotplates and the temperature range of interest. Heat conduction through tethers, heat conduction through the membrane, and heat conduction to the ambient air are given by $$Q_{Cond,Tethers} = \frac{4\left(\sum_{i=1}^{n} k_i T_i\right) W}{L_T} \Delta\Theta, \tag{1}$$

$$Q_{Cond,Membrane} = \frac{2\pi k_M T_M}{\ln(r_M / r_H)} \Delta\Theta, \text{ and} \tag{2}$$

$$Q_{Cond,Air} = \frac{4\pi k_{Air}}{1/r_I - 1/r_O} \Delta\Theta, \text{ respectively,} \tag{3}$$

where
$r_M = (L_M^2/\pi)^{0.5}$, $r_H = (L_H^2/\pi)^{0.5}$, $r_I = (L_H^2/2\pi)^{0.5}$, and $r_O = (3L_M^2/2\pi)^{0.5}$.

When the hotplate is released from the top, heat conduction to the ambient air above and below the heater should be considered separately since the radii of each imaginary hemisphere are not identical. The following equations describe each of them:

$$Q_{Cond,AirTop} = \frac{2\pi k_{Air}}{1/r_I - 1/r_O} \Delta\Theta \tag{4}$$

$$Q_{Cond,AirBottom} = \frac{2\pi k_{Air}}{1/r_I - 1/r_{OB}} \Delta\Theta \tag{5}$$

where $r_{OB} = (3 g^2/2\pi)^{0.5}$. However, when $g \ll L_H$, a thermal resistance should be included that accounts for rarefied gas conduction.

Using each heat transfer contribution, an energy balance for the micro hotplate can be formulated. For example, the energy balance for type C hotplate can be given by:

$$P = \frac{4\left(\sum_{i=1}^{n} k_i T_i\right) W}{L_T} \Delta\Theta + \frac{4\pi k_{Air}}{1/r_I - 1/r_O} \Delta\Theta. \tag{6}$$

Thermal resistance (or heating efficiency—temperature increase with a given power) can be given by:

$$R_{th} = \frac{\Delta\Theta}{P} = \left(\frac{4\left(\sum_{i=1}^{n} k_i T_i\right) W}{L_T} + \frac{4\pi k_{Air}}{1/r_I - 1/r_O}\right)^{-1}. \tag{7}$$

By introducing $\chi = L_H/L_M$, (7) can be rewritten as $$R_{th} = \frac{\Delta\Theta}{P} \tag{8}$$

$$= \frac{L_M(1-\chi)(\sqrt{3}-\chi)}{4\sqrt{2}\left(\sum_{i=1}^{n} k_i T_i\right) W(\sqrt{3}-\chi) + 2\sqrt{6\pi}\, k_{Air} L_m^2 \chi(1-\chi)}$$

The time constant of the system can be defined either in time or frequency domain. In time domain, most common definition is $\tau$ based on exponential temperature change that follows $1-\exp(-t/\tau)$ so that time constant is the time corresponding to about 63% of the final steady state temperature. More conservative definitions such as $2\tau$ or $3\tau$ can be used or time spent from 10 to 90% of the steady state temperature was used in. $\tau$ is used in the time domain as the response time of the hotplate hereafter.

To obtain time constants of this hotplate, a transient energy balance needs to be considered with a constant current source, I, as follows:

$$C\frac{d\Delta\Theta}{dt} + \frac{\Delta\Theta}{R_{th}} = I^2 R_0 (1 + \alpha \Delta\Theta). \tag{9}$$

In (9), higher order terms in temperature dependent electrical resistance can be neglected at low temperatures. After rearranging (9), the time constant during a heating cycle can be obtained as:

$$\tau_H = \left(\frac{1}{R_{th}} - I^2 R_0 \alpha\right)^{-1} C = \frac{R_{th} C}{1 - I^2 R_0 \alpha R_{th}}. \tag{10}$$

For a cooling cycle without electrical current, the right hand side of (9) becomes zero, thus a cooling time constant can be given by:

$$\tau_C = R_{th} C \tag{11}.$$

From (8), (10) and (11), it is obvious that there is a competition between heating efficiency and response time since both heating and cooling time constants tend to increase with increasing thermal resistance which is a measure of heating efficiency.

A similar analysis can be done for other micro hotplate types with corresponding thermal resistance, $R_{th}$. FIG. 15 summarizes energy balance and characteristics of the three hotplate types, where each hotplate type has a silicon nitride passivation layer above the heater and a silicon dioxide layer below the heater.

Using the above formulations, three types of the hotplate can be compared. FIG. 16(a) shows the heater power dissipation for three different types as a function of the heater temperature. Hereafter $L_M$ is 400 μm, g is 200 μm, $L_H$ is 100 μm, $T_{Si}$ is 0.34 μm, $T_{Si_3N_4}$ is 0.4 μm, $T_{SiO_2}$ is 0.4 μm, and $\Theta_0$ is 300 K unless otherwise noted.

The heater of the type B hotplate sits on a silicon dioxide membrane of which thickness is same as $T_{SiO_2}$ and thermophysical properties used are based on Table I. The heat transfer model predicts that type C hotplate requires smallest power to reach a target temperature and type B hotplate consumes higher power than other types for given geometries. However, type A can require more power than type B when the air gap, g, is sufficiently small. The Type C hotplate is always more efficient than type A or B, and is chosen for further design consideration. The inset of FIG. 16(a) compares conduction through four tethers and conduction to the air for the type C hotplate. When the heater temperature is 400 K, $Q_{Cond,Air}/Q_{Cond,Tethers}=2.51$. $Q_{Cond,Air}/Q_{Cond,Tethers}$ increases with increasing heater temperature since the thermal conductivity of the tether decreases but thermal conductivity of air increases with increasing temperature. FIG. 16(b) shows thermal resistance as a function of heater length to membrane length ratio, $\chi$, for various widths of the tether where the heater temperature is 400 K. As $\chi$ increases, thermal resistance decreases. For a given $\chi$, thermal resistance decreases with increasing tether width. Therefore, a small heater with narrow tethers can improve heating efficiency for a given membrane size.

Next, thermal response times, $\tau$, for the type C hotplate are considered using the transient energy balance. From (10) and (11), the heating time depends on not only thermal resistance and capacitance of the hotplate but also magnitude of electrical current, electrical resistance at reference temperature, and the temperature coefficient of electrical resistance (TCR) when the hotplate is resistively heated with a constant current source. However, the cooling time constant only depends on thermal resistance and capacitance of the hotplate when there is no electrical current. FIGS. 16(c) and 16(d) show heating and cooling time constant of the type C hotplate as a function of heater length to membrane length ratio for various widths of the tether where the hotplate temperature either increases or decreases between 300 and 400 K. For heating time constant, electrical current is 1 mA, electrical resistance at 300 K is 2 kΩ, and TCR is 1500 ppm/K and these values are kept constant even for different geometries. Both time constants increase as $\chi$ increases and the tether width decreases. For a given geometry, cooling is always faster than heating. Overall, a smaller micro hotplate will exhibit superior heating efficiency and faster response time. Narrow and long tethers are expected to increase $Q_{Cond,Air}/Q_{Cond,Tethers}$ and thus improve temperature uniformity in the heater. However, the width of the tether still offers a trade-off between the heating efficiency and the time constant.

TABLE I

Temperature dependent properties

|     |              | 300 K   | 400 K  | 600 K  | 800 K  |
|-----|--------------|---------|--------|--------|--------|
| Si  | k [W/m · K]  | 105.455 | 74.62  | 45.829 | 32.248 |
|     | c [kJ/kg · K]| 712     | 790    | 867    | 913    |
|     | ρ [kg/m³]    | 2330    | 2330   | 2330   | 2330   |
| SiO₂| k [W/m · K]  | 1.38    | 1.51   | 1.75   | 2.17   |
|     | c [kJ/kg · K]| 745     | 905    | 1040   | 1105   |
|     | ρ [kg/m³]    | 2220    | 2220   | 2220   | 2220   |
| Si₃N₄| k [W/m · K] | 16      | 13.9   | 11.3   | 9.88   |
|     | c [kJ/kg · K]| 691     | 778    | 937    | 1063   |
|     | ρ [kg/m³]    | 2400    | 2400   | 2400   | 2400   |
| Air | k [W/m · K]  | 0.0263  | 0.0338 | 0.0469 | 0.0573 |
|     | c [kJ/kg · K]| 1007    | 1014   | 1051   | 1099   |
|     | ρ [kg/m³]    | 1.1614  | 0.8711 | 0.5804 | 0.4354 |

It is also important to examine temperature dependent thermal resistance and time constant. FIGS. 17(a) and 17(b) show predicted thermal resistance and cooling time constant of the type C hotplate as a function of the heater temperature for various ratios of heater length to membrane length, where the tether width is 10 µm. Since the cooling time constant is independent of electrical properties or operating conditions, it can be considered as the more general thermal time constant for resistively-heated MEMS devices. The thermal resistance decreases as the heater temperature increases regardless of $\chi$. Since $Q_{Cond,Air}$ is the most dominant heat transfer mode, thermal resistance of the micro hotplate is dominated by the temperature dependent thermal conductivity of the air. However, the cooling time constant increases when $\chi<0.25$ but decreases when $\chi>0.25$ as the heater temperature increases, due to the interplay between temperature dependent thermal resistance and capacitance and their temperature derivatives. Based on the lumped heat transfer analysis and consideration of the sample mounting, geometries for the micro hotplate were determined and tabulated in Table II.

TABLE II

Micro hotplate geometries

|                  | $\chi = 0.25$ | $\chi = 0.5$ |
|------------------|---------------|--------------|
| $L_M$ [µm]       | 400           | 400          |
| $L_H$ [µm]       | 100           | 200          |
| $L_T$ [µm]       | 212           | 141          |
| $T_{Si}$ [µm]    | 0.34          | 0.34         |
| $T_{Si_3N_4}$ [µm]| 0.4          | 0.4          |
| $T_{SiO_2}$ [µm] | 0.4           | 0.4          |
| $W_H$ [µm]       | 10            | 10           |
| $W_T$ [µm]       | 5             | 10           |

C. Electrical Properties.

The electrical resistance of doped silicon resistors depends on the carrier mobility which is strong function of doping concentration and temperature. By employing bulk mobility models to the design shown in FIG. 14, the electrical resistance can be obtained. FIG. 18(a) shows predicted electrical resistance of the doped resistor L as a function of the heater temperature for different phosphorous doping concentrations. Electrical resistance of the resistor shows proportional trends and is not included here. At a given doping concentration, the electrical resistance increases at low temperatures and decreases at high temperatures as the heater temperature increases. This is due to the intrinsic carrier generation in the silicon and the turn-over point having maximum resistance is a characteristic of the doping concentration. The temperature corresponding to the turn-over point increases as the doping concentration increases.

To choose a doping concentration for the micro hotplate, electrical resistance and TCR must be considered since they affect thermal noise, heating time constant, and sensitivity of the resistive thermometer. FIG. 18(b) shows TCR and room temperature resistance of the resistor L as a function of phosphorous doping concentration. Room temperature resistance of the resistor L decreases with increasing doping concentration. TCR is calculated from the data shown in FIG. 18(a) as $(R_{L,500K}-R_{L,300K})/(R_{L,300K}\cdot 200)$. However, TCR decreases, exhibits a minimum, and increases as the doping concentration increases. High doping concentration is optimal in terms of thermal noise and heating time constant. In contrast, low doping concentration is optimal in terms of temperature sensing. To guarantee low thermal noise, fast heating time, and good temperature sensitivity, high doping concentration between $10^{20}$ and $10^{21}$/cm³ is recommended since TCR of the doped silicon resistor is comparable to that of metals even at high doping concentrations D. Mass Sensitivities.

For complementary gravimetric analyses, resonance characteristics of micro hotplates need to be considered. Based on the simple harmonic oscillator model, the resonance frequency of micro hotplates is proportional to $\sqrt{k/m}$, where k is the spring constant and m is the effective mass of micro hotplates. Since target analytes exhibit elastic modulus several orders of magnitude smaller than that of the structural materials of micro hotplates and small amount of analytes will be loaded only at the center membrane, resonance frequency shift at a given temperature is mainly attributed to the analyte mass change. Finite element modal analysis was performed to obtain resonance frequency and its mass dependence. The micro hotplate with 100 µm heater length has fundamental resonance frequency of 20.67 kHz and mass sensitivity of 356.4 Hz/ng and the micro hotplate with 200 µm heater length has fundamental resonance frequency of 18.13 kHz and mass sensitivity of 74.2 Hz/ng.

Fabrication.

FIGS. 5-9 shows the five major fabrication steps to make the micro hotplate for microDSC. The fabrication process started with a p-type silicon-on-insulator wafer (SOITEC) of orientation <100>, where the silicon device layer was 340 nm, the buried oxide (BOX) layer was 400 nm, and the silicon handle layer was 450 µm. Resistivity in the device layer was 14-22 Ω-cm. The tethered membrane structures were patterned first with a positive photoresist (Shipley, 1827) and etched into the silicon device layer using a Bosch process in an inductively coupled plasma (ICP) etcher. Then, an implantation step was performed with hard-baked positive photoresist (Shipley, 1827) as a mask for ion implantation. Exposed serpentine heater and tethers were doped with $2.51 \times 10^{16}$ cm$^{-2}$ of phosphorous at 180 keV. After selective implantation to define the heater, the photoresist implantation mask was removed with acetone and hot (120° C.) Piranah (70% $H_2SO_4$:30% $H_2O_2$ in volume ratio) solution. A 200 nm thick silicon dioxide layer was deposited on the entire wafer using plasma enhanced chemical vapor deposition (PECVD) to prevent dopants from diffusing back to the ambient during the subsequent heat treatment to anneal the damaged surface and further drive-in the dopants. The heat treatment was performed in a furnace tube for 50 min at 1000° C. and distributed dopants into the device layer. After the heat treatment, the PECVD oxide was removed in buffered oxide etch (BOE) to expose the doped silicon for metallization. Electron beam evaporation in conjunction with a lift-off process defined aluminum-doped silicon contacts, a 30-minute sintering step at 400° C. was performed to allow inter-diffusion of doped silicon and aluminum. Then, the backside of the wafer was patterned with a thick negative photoresist (Futurrex, NR5-8000) and etched using ICP. Finally, 400 nm of PECVD nitride was deposited on the front side for passivation. During backside ICP etch, two slender silicon bridges intended for snap-in release were left to hold each microDSC unit cell.

FIGS. 11(a) and 11(b) shows scanning electron micrographs of a typical fabricated micro hotplate having the heater length of 100 µm. In a microDSC unit cell, there are four identical micro hotplates so that any two of them can perform differential measurements. Each unit cell is wire-bonded to and packaged in a 28 pin dual-in-line package as shown in FIG. 11(c).

Characterization and Testing.

A. Electrical and Thermal Characterization.

As previously addressed, the fabricated micro hotplates have two doped silicon resistors each of which can be as either a heater or a resistive thermometer. First, they are operated as heaters. FIG. 19(a) shows the electrical resistance of the resistor L or the parallel resistor network of resistor L and resistor R as a function of the heater temperature at the center where both the resistor L and the parallel resistor network were connected to a sense resistor of ~8 kΩ. A micro hotplate having the heater length of 100 µm was used and the heater temperature at the center was measured with a laser Raman thermometry while the micro hotplate was Joule heated. When the resistor L was operated alone (configuration L), TCR was 1311 ppm/K in the temperature range of 300-500 K. When both resistors were operated (configuration L+R), TCR was 1254 ppm/K in the same temperature. Configuration L+R is expected to have better temperature uniformity than configuration L since Joule heating is more evenly distributed in configuration L+R than in configuration L. FIG. 19(b) shows the heater temperature at the center as a function of the heater power dissipation. Both configurations have similar thermal resistance of 36.7 K/mW in the temperature range of 300-400 K which shows a good agreement with the value of 40.6 K/mW from the lumped heat transfer model. As the lumped model predicted, the measured thermal resistance decreased with increasing heater temperature. At high temperatures, the thermal resistance for each configuration deviated and this is related to the temperature uniformity in the heater. In FIGS. 19(a) and 19(b), two micro hotplates (device 1 and 2) in a microDSC unit were used and their results agreed well enough for differential measurements.

Another possible operation is to use the resistor L as a heater and the resistor R as a resistive thermometer. FIG. 20(a) shows the heater temperature at the center ($T_c$) and electrical resistance of the resistor R ($R_R$) as a function of the heater power dissipation where a micro hotplate having the heater length of 200 µm is used. Again, measured thermal resistance of 18.3 K/mW showed a good agreement with the predicted value of 18.9 K/mW. TCR of the resistor R was 1312 ppm/K in the given temperature range. Both $T_c$ and $R_R$ showed linearity to the heater power dissipation for the tested range. Once $T_c$ is calibrated with $R_R$, the temperature of the micro hotplate can be monitored. FIG. 20(b) shows electrical resistance of the resistor R as a function of time when the square current pulse of 1.5 mA with 25 ms duration is applied to the resistor L. Heating and cooling time constants were 2.77 and 2.62 ms in the temperature range of 30-105° C., respectively, which were obtained from exponential growth/decay fits. Predicted heating and cooling time constants were 1.63 and 1.54 ms in the temperature range of 300-400 K with and without a constant current source, respectively. Measured time constants were somewhat greater than predicted ones possibly due to the underestimated heat capacity in the model prediction. Even though the micro hotplates were made of single crystal silicon for both structural and heater materials, their heating efficiency and response time are better than those of most micro hotplates previously reported. In addition, better temperature uniformity will be expected in the heater due to the relatively high thermal conductivity of silicon. Table III summarizes characteristics and performance of suspended micro hotplates published. The bottommost Si entry of Table III represents the micro hotplate described in this example.

TABLE III

| Heater material | Number of tethers | $L_M/L_T$ [µm] | $L_H$ [µm] | W/T [µm] | $\tau$ [ms] | $R_{th}$ [K/mW] |
|---|---|---|---|---|---|---|
| Poly-Si | 4 | 200/— | 100 | — | 0.6 | 8 |
| Poly-Si | 4 | —/110 | 100 | 20/5 | — | 11.7 (15 mW at 200° C.) |
| Si | 4 | —/— | — | —/— | 0.2 | 7.27~15 (11 mW at 350° C.) |
| Poly-Si | 4 | 200/— | 100 | 20/— | 3 (10 to 90%) | 23 (12 mW at 300° C.) |

TABLE III-continued

| Heater material | Number of tethers | $L_M/L_T$ [μm] | $L_H$ [μm] | W/T [μm] | $\tau$ [ms] | $R_{th}$ [K/mW] |
|---|---|---|---|---|---|---|
| Poly-Si | 4 | 200/— | 100 | —/— | 2-5 | 8 |
| HfB$_2$, SiC | 6 | —/100~150 | 100 | 10~40/— | <1 | 50 mW at 500° C. |
| HfB$_2$, SiC | 6 | —/100 | 100 | 10, 20, 40/— | — | 35 mW at 400° C. |
| Pt | 2 | —/— | 100 | —/— | 1.144 4.2 to 500° C. | 18 mW at 500° C. |
| Pt, Si | 2 | —/90 | 100 | 20/1 | — | 20 mW 550° C. |
| Poly-Si | 6 | —/98, 70 | 88 | 20, 10, 8/— | — | — |
| Poly-Si, Pt | 4 | —/100 | 100 | 25/4 | — | 20 |
| Pt | 4 | 1000/— | 400 | 60/~1.5 | 10 to 400° C. | 50 mW at 400° C. |
| Pt | 12 | —/— | 640 × 240 | —/— | — | 100 mW at 400° C. |
| Pt | 4 | 400/— | 190 | —/— | — | 18.2 (15.5 mW at 300° C.) |
| Pt | 4 | 400/177 | 150 | 30/~2 | — | 8.43 (30 mW at 550K) |
| Pt | 4 | —/210 | 500 | 70/~2 | 5.2 | — |
| Pt | 2 | —/— | 100 | —/— | — | 41.7 |
| Si | 4 | 400 | 100 200 | 10/0.34 | 1.5~1.7 2.6~2.8 | 36.7 18.3 |

B. Calorimetric Measurements.

Figure 21:
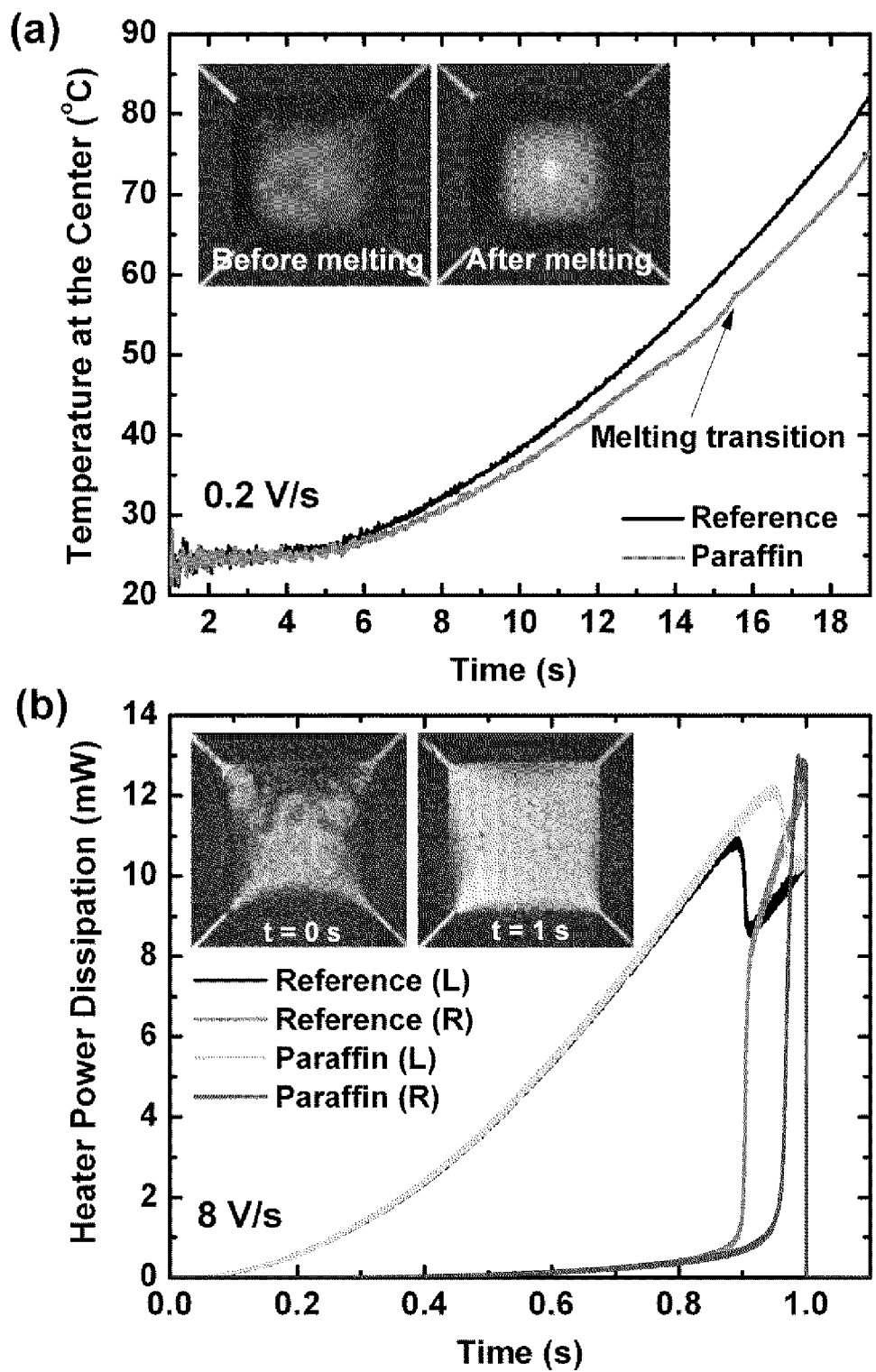
FIG. 21 illustrates data showing (a) Heater-thermometer temperatures of reference and paraffin-loaded micro hotplates with a slow linear voltage ramp of 0.2 V/s and (b) Heater-thermometer power dissipation with a fast linear voltage ramp of 8 V/s.

Following characterization, DSC measurements were performed on an analyte of paraffin wax. A wire-bonding machine was used for paraffin loading on the micro hotplate. FIG. 21(*a*) shows the heater temperature at the center as a function of time with and without the paraffin sample, respectively, where a slow linear voltage ramp of 0.2 V/s is applied. This differential measurement rejected common-mode signals. Paraffin melting transition was observed around t=15 s and optical micrographs confirmed the transition. Heater temperature of the paraffin loaded calorimeter at t=15 s is about 55° C. which is very close to the melting point of the paraffin sample (Fisher Scientific, P31-500), which ranges 53-57° C. To construct a calorimetric curve, a micro hotplate pair temperature is recommended to operate with feedback loops to maintain a same temperature both for reference and sample micro hotplates. FIG. 21(*b*) shows heater power dissipation as a function of time with a fast linear voltage ramp of 8 V/s. Loaded paraffin shown in the inset of FIG. 21(*b*) was completely consumed in a single heating cycle of 1 s duration. Since the heater was heated above thermal runaway of the intrinsic silicon, electrical crosstalk between the heater and the temperature sensor could exist; thus voltage and current in both resistors were monitored. By subtracting total power dissipation in the paraffin-loaded hotplate from that in the reference hotplate, thermal energy of 0.317 mJ associated with the performed calorimetric test was extracted using $$E = \int_0^t \sum_{L,R} (P_{Reference} - P_{Paraffin}) dt. \quad (12)$$

Several measurements were repeated with varying initial paraffin mass on the micro hotplate and the extracted energy was somewhat proportional to the initial paraffin mass. The energy was attributed to the combination of sensible and latent heats since the micro hotplate underwent a wide range of temperature change.

Figure 22:
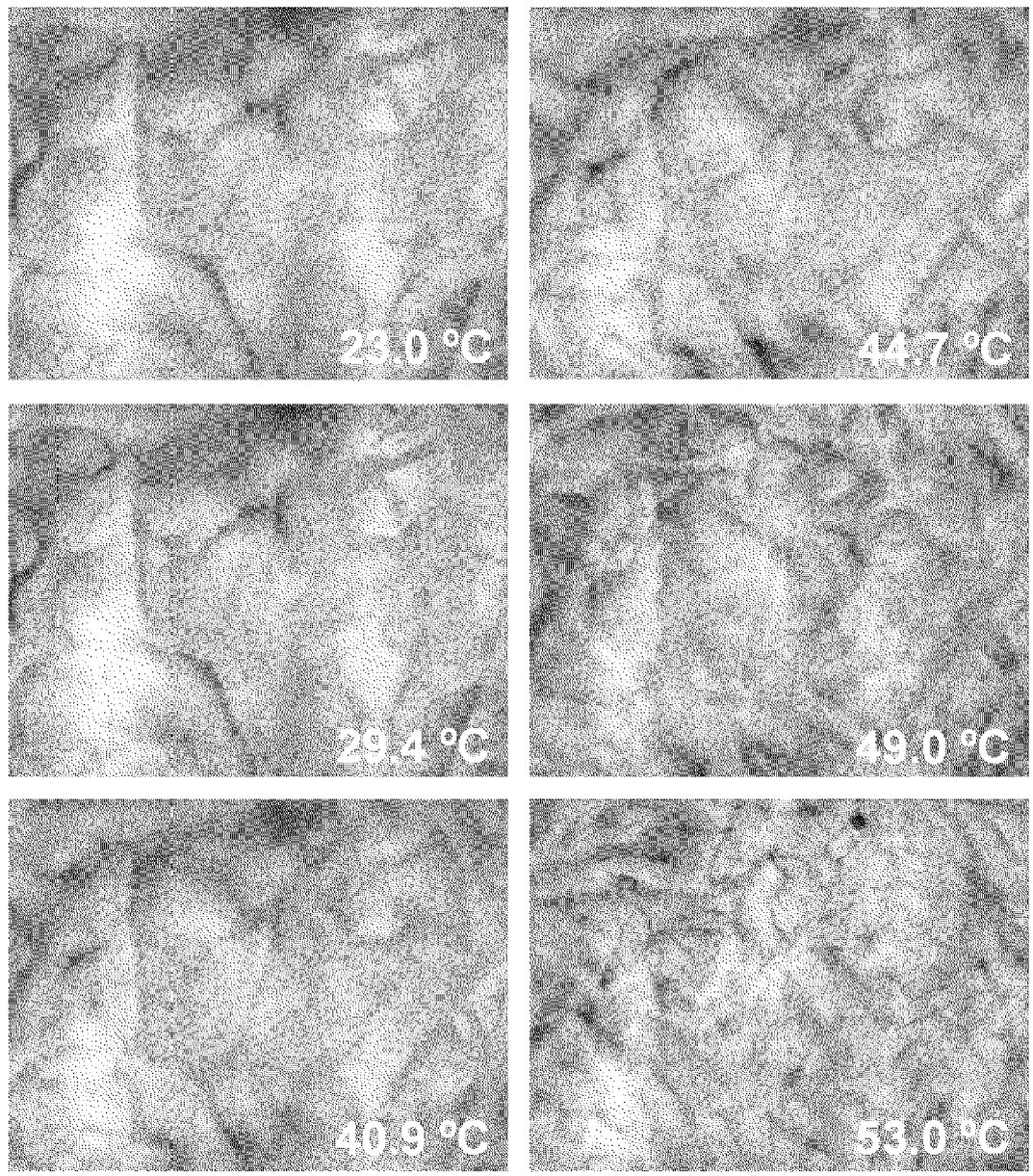
FIG. 22 shows Optical microscopy and Raman spectroscopy data for a parrafin loaded micro calorimeter at a variety of temperatures.
Figure 22:
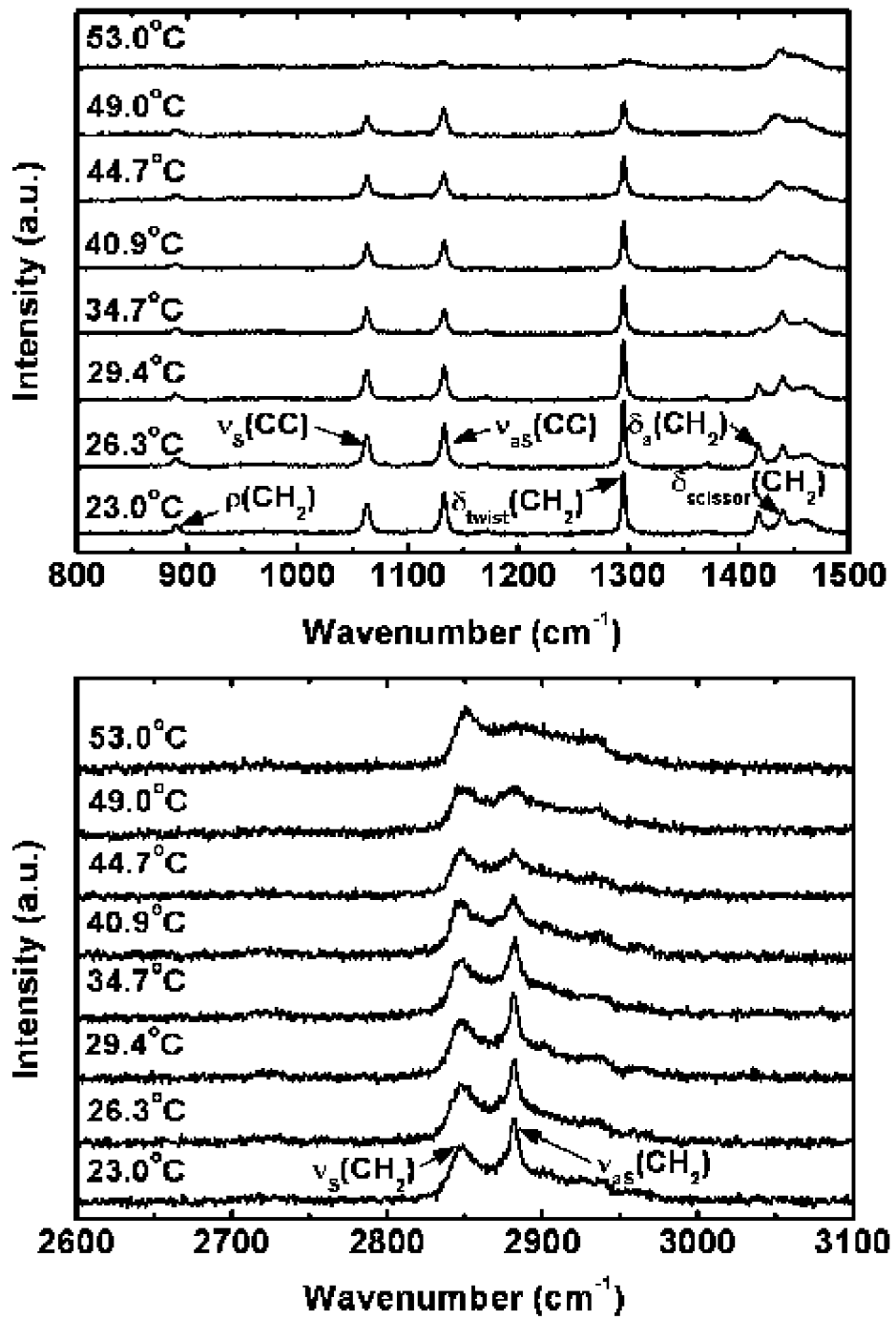

MicroDSC consumes orders of magnitude reduced amount of a sample, offers fast operation, and provides improved sensitivity. In addition, microDSC facilitates integration of other optical and spectroscopic diagnostic tools due to its small size and highly localized heating. Although there are growing needs to combine DSC with optical microscope, Fourier transform infrared (FTIR) spectroscopy, and Raman spectroscopy, there was little effort to build such simultaneous thermal and chemical analysis tools using a microDSC. The micro hotplate described in this example can be easily integrated with optical microscopes or vibration spectroscopes without any modification. FIG. 22 shows optical micrographs and Raman spectra of the paraffin at different heater temperatures when the micro hotplate is Joule heated with a dc voltage source. Either optical micrographs or Raman spectra could provide information regarding structural changes upon thermal transition events. The results suggest a cost-effective solution for simultaneous DSC and optical measurements.

List Of Symbols

C: Heat capacity
c: Specific heat
E: Energy
g: Air gap between the hotplate and bulk material
I: Electrical current
k: Thermal conductivity
L: Length
P: Power generated via Joule heating
Q: Heat energy
R: Resistance
r: Radius
T: Thickness
t: Time
V: Voltage
W: Width
α: Temperature coefficient of the resistance (TCR)
χ: Heater length to membrane length ratio
Θ: Temperature
ρ: Density Subscripts 0: Reference temperature
C: Cooling
c: Center
Cond: Conduction
Gen: Generation
H: Heater or heating
I: Inner imaginary sphere
i: Index for constituent materials for hotplate
L: Left
M: Membrane
O: Outer imaginary sphere OB: Outer imaginary hemi-sphere at the bottom
OT: Outer imaginary hemi-sphere at the top
R: Right
T: Tether
th: Thermal
W: Wafer Figure Captions:

FIG. 14. Design of the microfabricated hotplate calorimeter. A squared island exists at the center linked to the bulk silicon chip with four tethers. Two serpentine heater-thermometer tracks run through the island that will serve as a heater platform. Each doped silicon can be used either a heater or a resistive thermometer.

FIG. 15. Lumped heat transfer model and characteristics of three micro hotplate types. Type A is a suspended membrane micro hotplate released from the top side, type B is a micro hotplate sitting on a dielectric closed membrane released from the bottom side, and type C is a suspended membrane micro hotplate released from the bottom side. Each model has an identical heater and tether geometry. In lumped heat transfer mode, thermal radiation can be neglected when the heater temperature is lower than 800 K.

Figure 16:
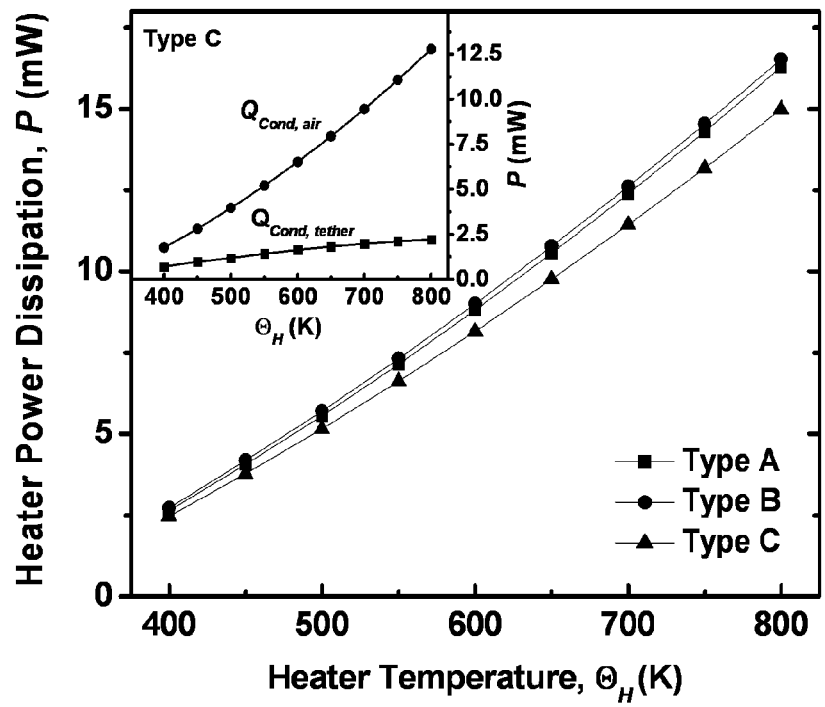
FIG. 16 illustrates data showing the thermal behaviors of a micro hotplate predicted by the lumped heat transfer analysis.
Figure 16:
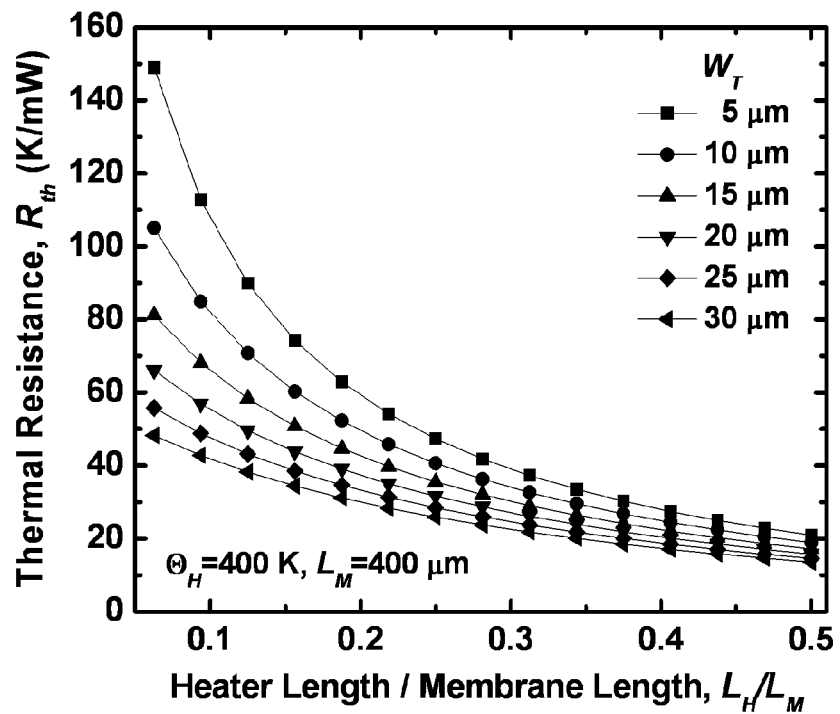
Figure 16:
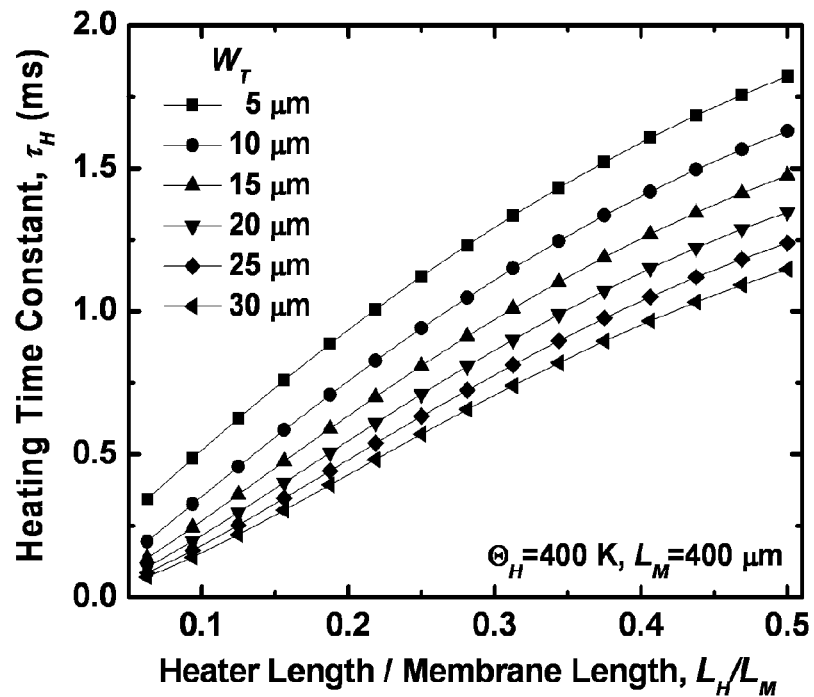
Figure 16:
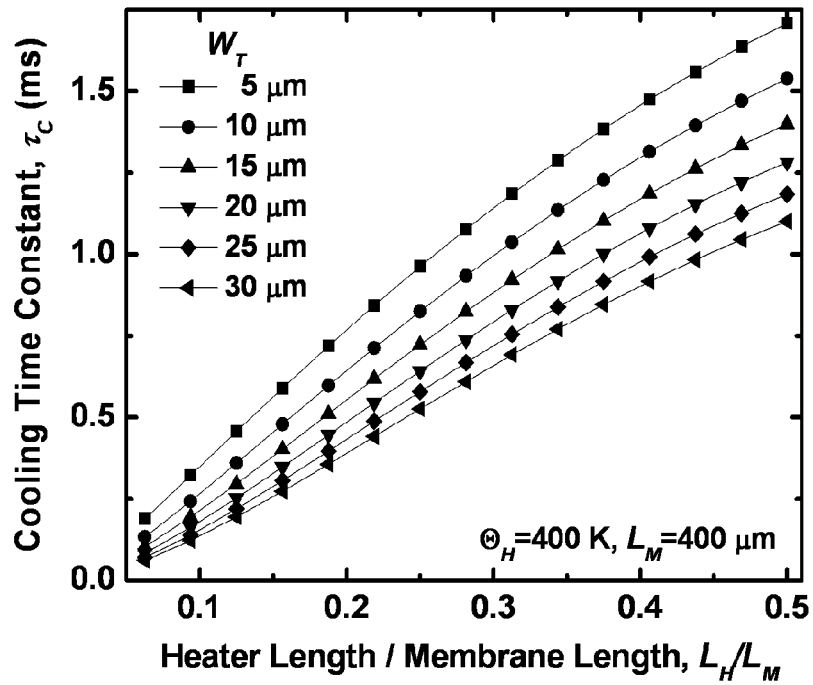

FIG. 16. Thermal behaviors of micro hotplate predicted by the lumped heat transfer analysis. (a) Heater power dissipation as a function of the heater temperature indicating type C has the best heating efficiency. Inset shows two major heat transfer contribution of the type C micro hotplate. Only type C is considered from hereinafter. (b) Thermal resistance (heating efficiency), (c) heating time constant, and (d) cooling time constant as a function of the heater length-to-membrane length ratio ($\chi$=LH/LM) with various tether width ranging from 5 to 30 µm, respectively. Thermal resistance decreases as either heater length-to-membrane length ratio or tether width increases. In contrast, time constant (both heating and cooling) show the opposite trend. Membrane length of 400 µm and heater temperature of 400 K are used.

Figure 17:
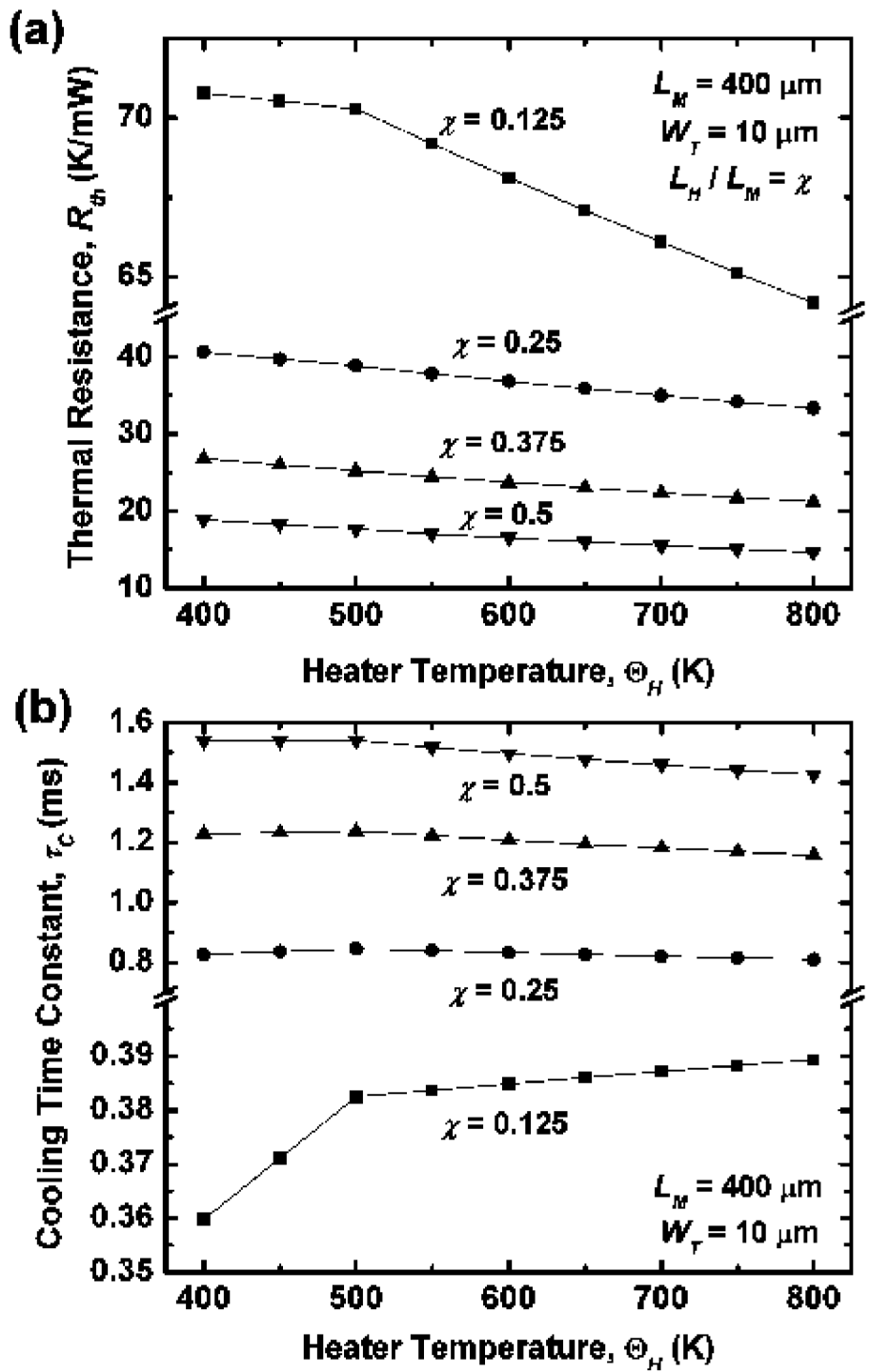
FIG. 17 illustrates data showing (a) Thermal resistance and (b) cooling time constant as a function of the heater temperature for various micro calorimeter geometries.

FIG. 17. (a) Thermal resistance and (b) cooling time constant as a function of the heater temperature with various $\chi$=LH/LM. Thermal resistance decreases with increasing heater temperature regardless of $\chi$. However, cooling time constant decreases with $\chi$ greater than 0.25 and increases with $\chi$ smaller than 0.25. This is due to the interplay of temperature dependent thermal resistance and time constant, and their temperature derivatives.

Figure 18:
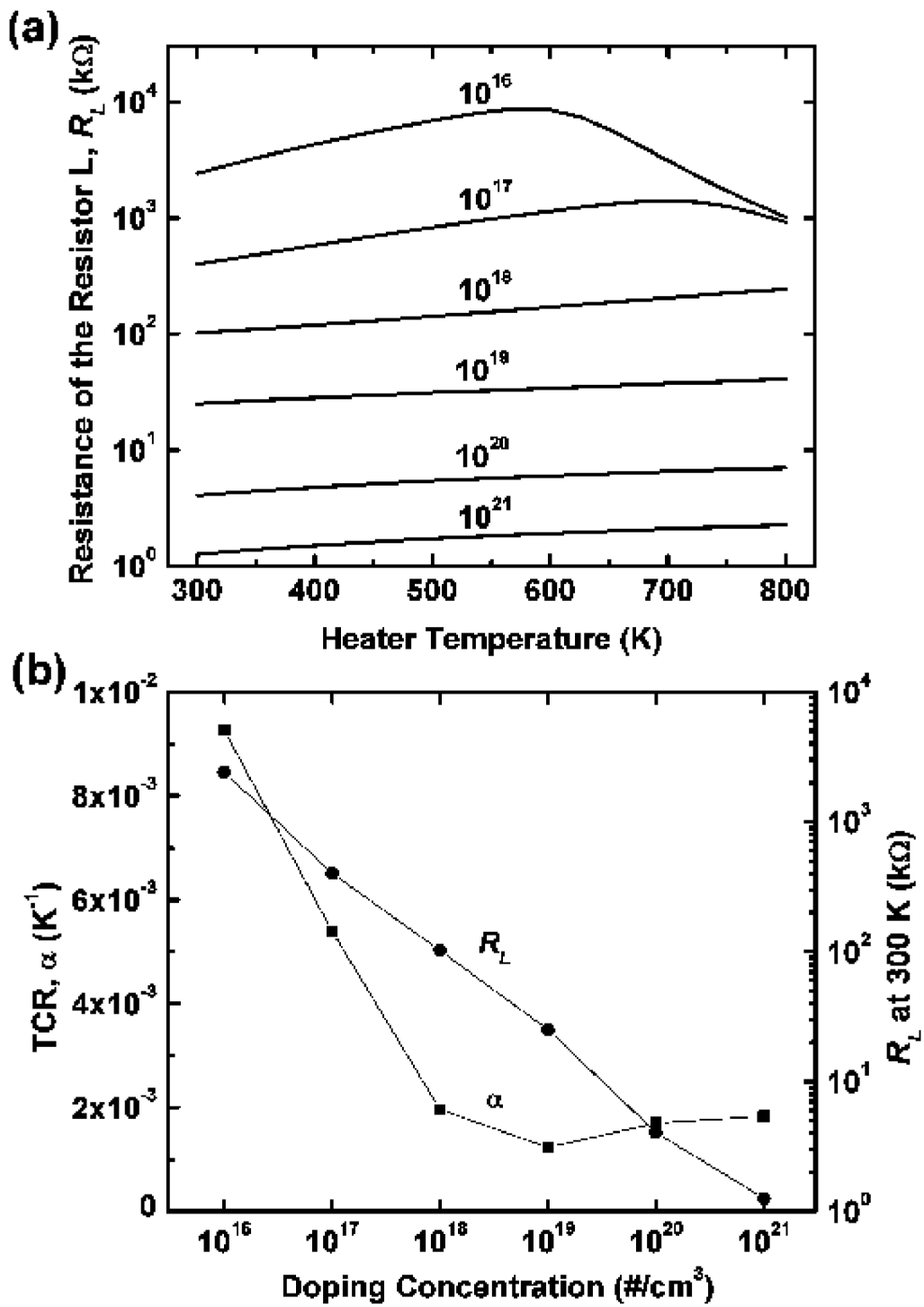
FIG. 18 illustrates data showing (a) Heater resistance as a function of temperature for a variety of dopant concentrations and (b) Temperature coefficient of electrical resistance and resistance of the heater-thermometer at 300 K as a function of dopant concentration.

FIG. 18. (a) Heater resistance as a function of temperature at different doping (phosphorous) concentrations. (b) Temperature coefficient of electrical resistance and resistance of the resistor L at 300 K (right y-axis) as a function of doping concentration.

Figure 11:
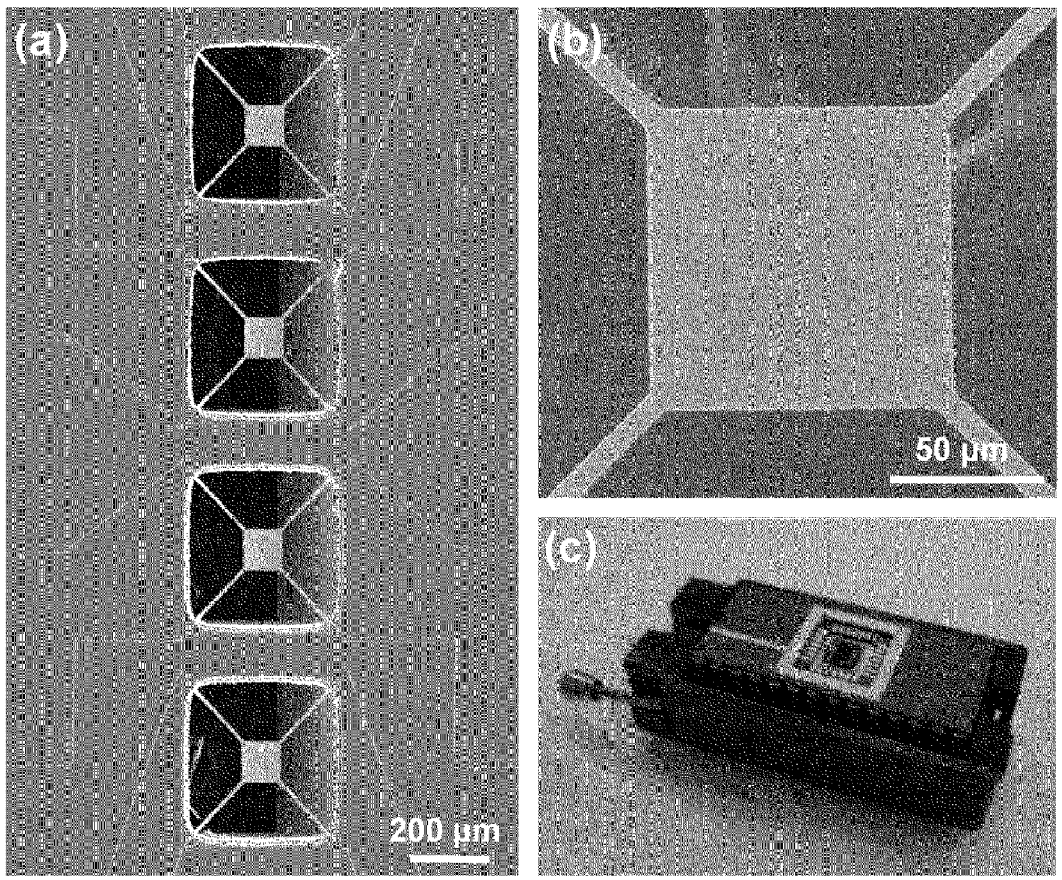
FIG. 11a shows a scanning electron micrograph image of four micro calorimeters.
FIG. 11b shows an expanded scanning electron micrograph image of one micro calorimeter.
FIG. 11c shows a 28 pin dual-in-line package where each micro calorimeter unit cell is wire-bonded for external electrical connections.

FIG. 11. Scanning electron micrographs of a fabricated microcalorimeter. (a) A differential scanning calorimeter (DSC) unit die having four identical micro hotplates in a row. (b) A close up of one device. (c) A picture showing a microDSC unit attached to and wire-bonded to a dual-inline package.

Figure 19:
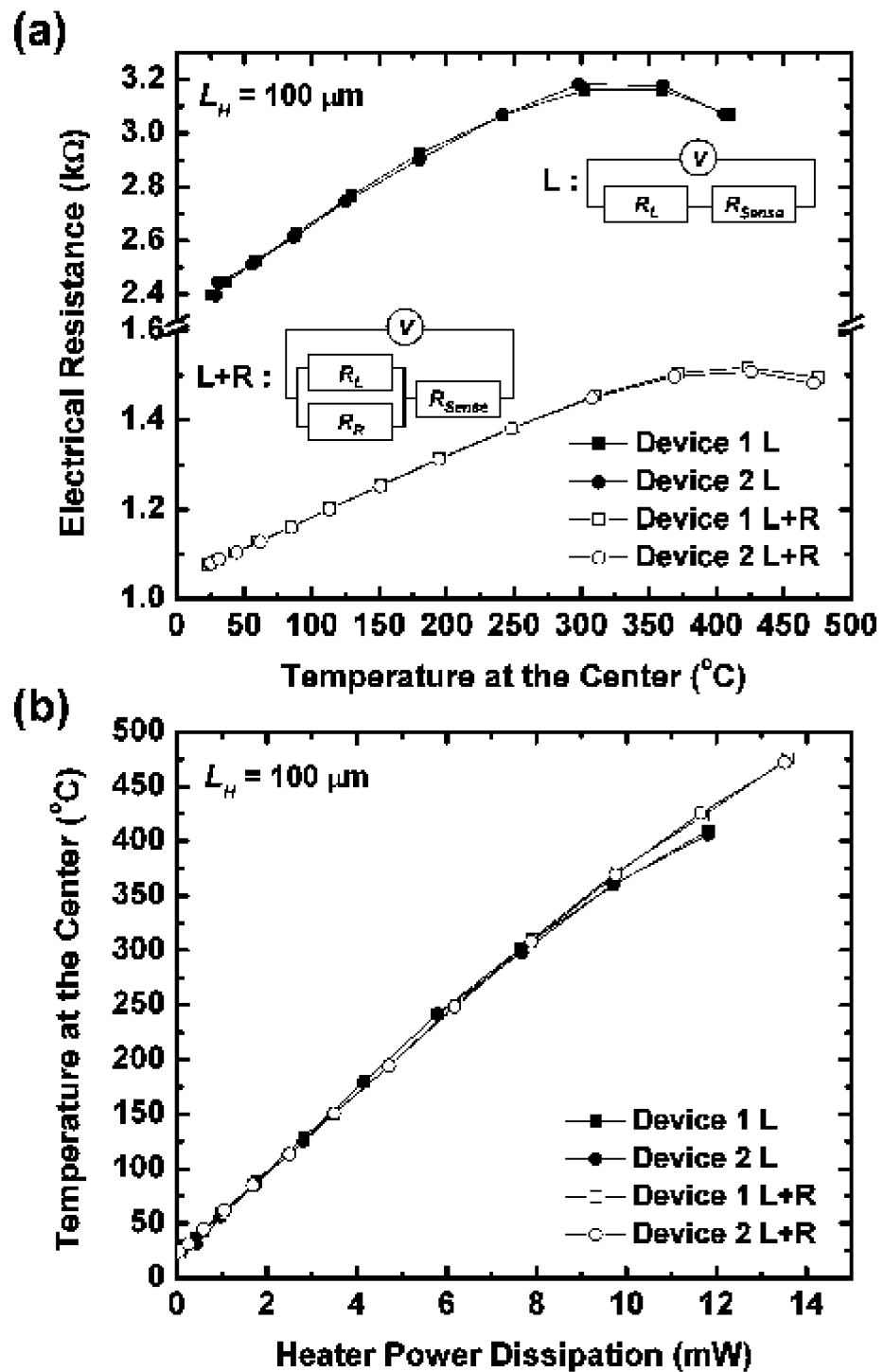
FIG. 19 illustrates data showing (a) Electrical resistance of heater-thermometers as a function of the temperature at the center of the heater-thermometer and (b) Temperature as the center of the heater as a function of the heater power dissipation for configurations having heating from two heater-thermometers.

FIG. 19. (a) Electrical resistance of the resistor L and the parallel resistor network of both resistors as a function of the temperature at the center of the heater. (b) Temperature as the center of the heater as a function of the heater power dissipation for two circuit configurations using both resistors as heaters. Temperature calibration is performed using a micro Raman spectroscopy. Two micro hotplate devices from a same unit die are used and their results are good enough for differential metrology.

Figure 20:
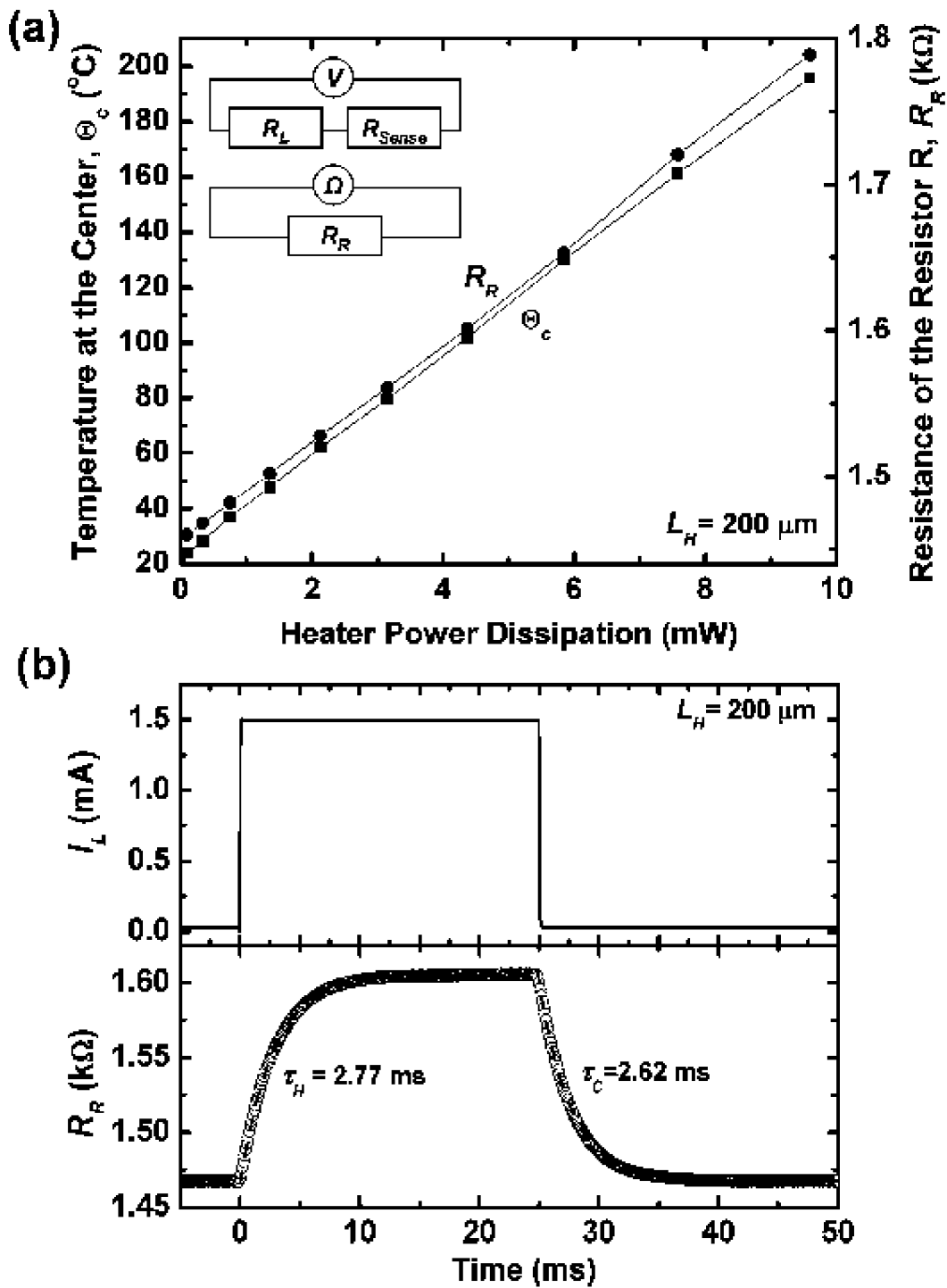
FIG. 20 illustrates data showing (a) Temperature at the center of a first heater-thermometer and electrical resistance of a second heater-thermometer as a function of the first heater-thermometer power dissipation and (b) Electrical resistance of the first heater-thermometer as a function of time when a square current pulse is applied to a second heater-thermometer.

FIG. 20. (a) Temperature at the center of the heater and electrical resistance of the resistor R as a function of the heater power dissipation (more specifically, power dissipated in the resistor L). Resistor L is used as a heater and resistor R is used a resistive thermometer in the given configuration. These linear temperature and thermometer resistance in the given power range facilitate temperature programming. (b) Electrical resistance of the resistor R as a function of time when a square current pulse is applied to the resistor L. Heating and cooling time constants are extracted using exponential growth/decay fits.

FIG. 21. (a) Heater temperatures of reference and paraffin-loaded micro hotplates with a slow linear voltage ramp of 0.2 V/s. Paraffin melting transition is about 55° C. and melting is confirmed with optical micrographs. Inset shows the paraffin-loaded micro hotplate before and after melting transition. (b) Heater power dissipation with a fast linear voltage ramp of 8 V/s. The paraffin loaded on the micro hotplate is completely consumed within 1 s and the thermal energy of 0.317 mJ associated with the performed calorimetric test is extracted.

FIG. 22. Optical microscopy and Raman spectroscopy combined with a micro hotplate DSC. Conformational change and specific band stretching can be studied while performing calorimetry which is not difficult to perform with conventional bench top DSC.

REFERENCES

E. A. Olson, M. Yu, Y. Efremov, M. Zhang, Z. S. Zhang, L. H. Allen, The design and operation of a MEMS differential scanning nanocalorimeter for high-speed heat capacity measurements of ultrathin films, Journal of Microelectromechanical Systems 12 (2003) 355-364.

M. Y. Efremov, E. A. Olson, M. Zhang, F. Schiettekatte, Z. S. Zhang, L. H. Allen, Ultrasensitive, fast, thin-film differential scanning calorimeter, Review of Scientific Instruments 75 (2004) 179-191.

J. Spannhake, A. Helwig, G. Muller, G. Faglia, G. Sberveglieri, T. Doll, T. Wassner, A. Eickhoff, $SnO_2$: Sb—A new material for high-temperature MEMS heater applications: Performance and limitations, Sensors and Actuators B-Chemical 124 (2007) 421-428.

D. W. Denlinger, E. N. Abarra, K. Allen, P. W. Rooney, M. T. Messer, S. K. Watson, and F. Hellman, "Thin-film microcalorimeter for heat-capacity measurements from 1.5 K to 800 K," Rev. Sci. Instrum., vol. 65, pp. 946-958, April 1994.

S. L. Lai, G. Ramanath, L. H. Allen, P. Infante, and Z. Ma, "High-speed (104° C./S) scanning microcalorimetry with monolayer sensitivity (J/m2)," Appl. Phys. Lett., vol. 67, pp. 1229-1231, Aug. 28, 1995.

S. L. Lai, J. Y. Guo, V. Petrova, G. Ramanath, and L. H. Allen, "Size-dependent melting properties of small tin particles: Nanocalorimetric measurements," Phys. Rev. Lett., vol. 77, pp. 99-102, Jul. 1, 1996.

S. L. Lai, J. R. A. Carlsson, and L. H. Allen, "Melting point depression of Al clusters generated during the early stages of film growth: Nanocalorimetry measurements," Appl. Phys. Lett., vol. 72, pp. 1098-1100, Mar. 2, 1998.

M. Zhang, M. Y. Efremov, F. Schiettekatte, E. A. Olson, A. T. Kwan, S. L. Lai, T. Wisleder, J. E. Greene, and L. H. Allen, "Size-dependent melting point depression of nanostructures: Nanocalorimetric measurements," Phys. Rev. B: Condens. Matter, vol. 62, pp. 10548-10557, Oct. 15, 2000.

E. A. Olson, M. Y. Efremov, M. Zhang, Z. Zhang, and L. H. Allen, "Size-dependent melting of Bi nanoparticles," J. Appl. Phys., vol. 97, p. 034304, Feb. 1, 2005.

L. H. Allen and S. L. Lai, "MEMS-based scanning calorimeter for thermodynamic properties of nanostructures," Microscale Thermophys. Eng., vol. 2, pp. 11-19, January-March 1998.

M. Y. Efremov, J. T. Warren, E. A. Olson, M. Zhang, A. T. Kwan, and L. H. Allen, "Thin-film differential scanning calorimetry: A new probe for assignment of the glass transition of ultrathin polymer films," Macromolecules, vol. 35, pp. 1481-1483, Feb. 26, 2002.

M. Y. Efremov, E. A. Olson, M. Zhang, Z. Zhang, and L. H. Allen, "Glass transition in ultrathin polymer films: calorimetric study," Phys. Rev. Lett., vol. 91, p. 085703, Aug. 22, 2003.

M. Y. Efremov, E. A. Olson, M. Zhang, and L. H. Allen, "Glass transition of thin films of poly(2-vinyl pyridine) and poly(methyl methacrylate): nanocalorimetry measurements," Thermochim. Acta, vol. 403, pp. 37-41, Jun. 26, 2003.

M. Y. Efremov, E. A. Olson, M. Zhang, Z. S. Zhang, and L. H. Allen, "Probing glass transition of ultrathin polymer films at a time scale of seconds using fast differential scanning calorimetry," Macromolecules, vol. 37, pp. 4607-4616, Jun. 15, 2004.

S. Zhang, Y. Rabin, Y. Yang, and M. Asheghi, "Nanoscale calorimetry using a suspended bridge configuration," J. Microelectromech. Syst., vol. 16, pp. 861-871, August 2007.

R. E. Cavicchi, G. E. Poirier, N. H. Tea, M. Afridi, D. Berning, A. Hefner, I. Suehle, M. Gaitan, S. Semancik, and C. Montgomery, "Micro-differential scanning calorimeter for combustible gas sensing," Sens. Actuators B, Chem., vol. 97, pp. 22-30, Jan. 1, 2004.

J. S. Suehle, R. E. Cavicchi, M. Gaitan, and S. Semancik, "Tin oxide gas sensor fabricated using CMOS micro-hotplates and insitu processing," IEEE Electron Device Lett., vol. 14, pp. 118-120, March 1993.

N. Najafi, K. D. Wise, and J. W. Schwank, "A Micromachined Ultra-Thin-Film Gas Detector," IEEE Trans. Electron. Devices, vol. 41, pp. 1770-1777, October 1994.

D. Beckel, D. Briand, A. Bieberle-Hutter, J. Courbat, N. F. de Rooij, and L. J. Gauckler, "Micro-hotplates—A platform for micro-solid oxide fuel cells," J. Power Sources, vol. 166, pp. 143-148, Mar. 30, 2007.

F. T. Zhang, Z. Tang, J. Yu, and R. C. Jin, "A micro-Pirani vacuum gauge based on micro-hotplate technology," Sens. Actuators A, Phys., vol. 126, pp. 300-305, Feb. 14, 2006.

D. C. Meier, C. J. Taylor, R. E. Cavicchi, V. E. White, M. W. Ellzy, K. B. Sumpter, and S. Semancik, "Chemical warfare agent detection using MEMS-compatible microsensor arrays," IEEE Sens. J., vol. 5, pp. 712-725, August 2005.

A. G. Shirke, R. E. Cavicchi, S. Semancik, R. H. Jackson, B. G. Frederick, and M. C. Wheeler, "Femtomolar isothermal desorption using microhotplate sensors," J. Vac. Sci. Technol., A, vol. 25, pp. 514-526, May-June 2007.

C. Washburn, M. W. Moorman, T. W. Hamilton, A. L. Robinson, C. Mowry, R. G. Manley, and G. Shelmidine, "Micro-flame ionization detection using a catalytic microcombuster," in 2005 IEEE Sensors, 2005, pp. 322-325.

M. Graf, R. Jurischka, D. Barrettino, and A. Hierlemann, "3D nonlinear modeling of microhotplates in CMOS technology for use as metal-oxide-based gas sensors," J. Micromech. Microeng., vol. 15, pp. 190-200, January 2005.

F. Udrea, J. W. Gardner, D. Setiadi, J. A. Covington, T. Dogaru, C. C. Lua, and W. I. Milne, "Design and simulations of SOICMOS micro-hotplate gas sensors," Sens. Actuators B, Chem., vol. 78, pp. 180-190, Aug. 30, 2001.

F. P. Incropera and D. P. DeWitt, Fundamentals of Heat and Mass Transfer, 5th ed. New York: J. Wiley, 2002.

F. Solzbacher, T. Doll, and E. Obermeier, "A comprehensive analytical and numerical analysis of transient and static micro hotplate characteristics," in Transducers '03, the 12th international conference on solid-state sensors, actuators and Microsystems, Boston, Mass., USA, 2003.

J. Lee, T. L. Wright, M. R. Abel, E. O. Sunden, A. Marchenkov, S. Graham, and W. P. King, "Thermal conduction from microcantilever heaters in partial vacuum," J. Appl. Phys., vol. 101, p. 014906, Jan. 1, 2007.

G. Sberveglieri, W. Hellmich, and G. Muller, "Silicon hotplates for metal oxide gas sensor elements," Microsyst. Tech., vol. 3, pp. 183-190, August 1997.

M. H. Han, X. G. Liang, and Z. A. Tang, "Size effect on heat transfer in micro gas sensors," Sens. Actuators A, Phys., vol. 120, pp. 397-402, May 17, 2005.

L. Y. Sheng, Z. N. Tang, J. Wu, P. C. H. Chan, and J. K. O. Sin, "A low-power CMOS compatible integrated gas sensor using maskless tin oxide sputtering," Sens. Actuators B, Chem., vol. 49, pp. 81-87, Jun. 25, 1998.

S. Reggiani, M. Valdinoci, L. Colalongo, M. Rudan, G. Baccarani, A. D. Stricker, F. Illien, N. Felber, W. Fichtner, and L. Zullino, "Electron and hole mobility in silicon at large operating temperatures—Part I: Bulk mobility," IEEE Trans. Electron Devices, vol. 49, pp. 490-499, March 2002.

B. W. Chui, M. Asheghi, Y. S. Ju, K. E. Goodson, T. W. Kenny, and H. J. Mamin, "Intrinsic-carrier thermal runaway in silicon microcantilevers," Microscale Thermophys. Eng., vol. 3, pp. 217-228, 1999.

J. Lee, T. Beechem, T. L. Wright, B. A. Nelson, S. Graham, and W. P. King, "Electrical, thermal, and mechanical characterization of silicon microcantilever heaters," J. Microelectromech. Syst., vol. 15, pp. 1644-1655, December 2006.

J. Lee and W. P. King, "Microthermogravimetry using a microcantilever hotplate with integrated temperature compensated piezoresistive strain sensors," Rev. Sci. Instrum., vol. 79, p. 054901, 2008.

J. M. Hey, P. M. Mehl, and D. R. MacFarlane, "A combined differential scanning calorimeter optical video microscope for crystallization studies," J. Therm. Anal., vol. 49, pp. 991-998, 1997.

D. J. Johnson, D. A. C. Compton, and P. L. Canale, "Applications of Simultaneous Dsc Ftir Analysis," Thermochim. Acta, vol. 195, pp. 5-20, Jan. 17, 1992.

B. Degamber, D. Winter, J. Tetlow, M. Teagle, and G. F. Fernando, "Simultaneous DSC/FTIRS/TMA," Meas. Sci. Technol., vol. 15, pp. L5-L10, September 2004.

J. C. Sprunt and U. A. Jayasooriya, "Simultaneous FT-Raman differential scanning calorimetry measurements using a low-cost fiber-optic probe," Appl. Spectrosc., vol. 51, pp. 1410-1414, September 1997.

B. W. Chui, T. D. Stowe, Y. S. Ju, K. E. Goodson, T. W. Kenny, H. J. Mamin, B. D. Terris, and R. P. Ried, "Low-stiffness silicon cantilever with integrated heaters and piezoresistive sensors for high-density data storage," J. Microelectromech. Syst., vol. 7, pp. 69-78, 1998.

C. Dücso, É. Vázsonyi, M. Ádám, I. Szabó, I. Bársony, J. G. E. Gardeniers, and A. van den Berg, "Porous silicon bulk micromachining for thermally isolated membrane formation," Sens. Actuators A, Phys., vol. 60, pp. 235-239, May 1997.

S. K. H. Fung, Z. N. Tang, P. C. H. Chan, J. K. O. Sin, and P. W. Cheung, "Thermal analysis and design of a micro-hotplate for integrated gas-sensor applications," Sens. Actuators A, Phys., vol. 54, pp. 482-487, June 1996.

S. Semancik and R. Cavicchi, "Kinetically controlled chemical sensing using micromachined structures," Acc. Chem. Res., vol. 31, pp. 279-287, 1998.

F. Solzbacher, T. Doll, and E. Obermeier, "A comprehensive analytical and numerical analysis of transient and static micro hotplate characteristics," in The 12th International Conference on Solid State Sensors, Actuators, and Microsystems, Boston, 2003, pp. 1856-1859.

F. Solzbacher, C. Imawan, H. Steffes, E. Obermeier, and H. Möller, "A modular system of SiC-based microhotplates for the application in metal oxide gas sensors," Sens. Actuators B, Chem., vol. 64, pp. 95-101, Jun. 10, 2000.

P. Fürjes, C. Dücsö, M. Ádám, J. Zettner, and I. Bársony, "Thermal characterisation of micro-hotplates used in sensor structures," Superlattices Microstruct., vol. 35, pp. 455-464, March-June 2004.

P. Furies, Z. Vízváry, M. Ádám, I. Bársony, A. Morrissey, and C. Dücsö, "Materials and processing for realization of micro-hotplates operated at elevated temperature," J. Micromech. Microeng., vol. 12, pp. 425-429, July 2002.

C. Tsamis, A. G. Nassiopoulou, and A. Tserepi, "Thermal properties of suspended porous silicon micro-hotplates for sensor applications," Sens. Actuators B, Chem., vol. 95, pp. 78-82, Oct. 15, 2003.

J. C. Belmonte, J. Puigcorbe, J. Arbiol, A. Vila, J. R. Morante, N. Sabate, I. Gracia, and C. Cane, "High-temperature low-power performing micromachined suspended micro-hotplate for gas sensing applications," Sens. Actuators B, Chem., vol. 114, pp. 826-835, Apr. 26, 2006.

D. S. Lee, C. H. Shim, J. W. Lim, J. S. Huh, D. D. Lee, and Y. T. Kim, "A microsensor array with porous tin oxide thin films and microhotplate dangled by wires in air," Sens. Actuators B, Chem., vol. 83, pp. 250-255, Mar. 15, 2002.

G. Guo, A. Bermak, P. C. H. Chan, and G. Z. Yan, "A monolithic integrated 4×4 tin oxide gas sensor array with on-chip multiplexing and differential readout circuits," Solid-State Electron., vol. 51, pp. 69-76, January 2007.

I. Hotovy, V. Rehacek, F. Mika, T. Lalinsky, S. Hascik, G. Vanko, and M. Drzik, "Gallium arsenide suspended microheater for MEMS sensor arrays," Microsyst. Tech., vol. 14, pp. 629-635, April 2008.

G. Wiche, A. Berns, H. Steffes, and E. Obermeier, "Thermal analysis of silicon carbide based micro hotplates for metal oxide gas sensors," Sens. Actuators A, Phys., vol. 123-24, pp. 12-17, Sep. 23, 2005.

P. Füries, Z. Vízváry, M. Ádám, A. Morrissey, C. Dücsö, and I. Bársony, "Thermal investigation of micro-filament heaters," Sens. Actuators A, Phys., vol. 99, pp. 98-103, Apr. 30, 2002.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "having," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A microcalorimeter comprising a single crystal silicon suspended structure supported by one or more single crystal silicon tethers, wherein the single crystal silicon suspended structure comprises a heater-thermometer, wherein the heater-thermometer comprises a region of doped single crystal silicon within the single crystal silicon suspended structure, wherein the single crystal silicon suspended structure and heater-thermometer comprise a unitary structure and wherein the heater-thermometer provides both heating and temperature sensing in a single element comprising said region of doped single crystal silicon.

2. The microcalorimeter of claim 1, wherein the single crystal silicon suspended structure and heater-thermometer comprise a single layer.

3. The microcalorimeter of claim 1, wherein the single crystal silicon suspended structure has a planar surface.

4. The microcalorimeter of claim 1, wherein the single crystal silicon suspended structure is a suspended platform.

5. The microcalorimeter of claim 1, wherein the single crystal silicon suspended structure has a width selected from the range of 10 to 500 µm.

6. The microcalorimeter of claim 1, wherein the heater-thermometer comprises a serpentine path across the single crystal silicon suspended structure.

7. The microcalorimeter of claim 1, comprising four single crystal silicon tethers.

8. The microcalorimeter of claim 1, wherein at least one single crystal silicon tether comprises doped single crystal silicon.

9. The microcalorimeter of claim 1, wherein the one or more single crystal silicon tethers have a width selected from the range of 1 to 50 µm.

10. The microcalorimeter of claim 1, wherein the one or more single crystal silicon tethers have a length selected from the range of 10 to 500 µm.

11. The microcalorimeter of claim 1, wherein the one or more single crystal silicon tethers have a thickness selected from the range of 0.05 to 5.0 µm.

12. The microcalorimeter of claim 1, further comprising a resistance measuring circuit electrically connected to the heater-thermometer for measuring a resistance of the heater-thermometer.

13. The microcalorimeter of claim 1, further comprising a current source electrically connected to the heater-thermometer for providing a current to the heater-thermometer.

14. A method of making a calorimetric measurement, the method comprising:
provoding a microcalorimeter comprising a single crystal silicon suspended structure supported by one or more single crystal silicon tethers, wherein the single crystal silicon suspended structure comprises a heater-thermometer, wherein the heater-thermometer comprises a region of doped single crystal silicon within the single crystal silicon suspended structure, wherein the single crystal silicon suspended structure and heater-thermometer comprise a unitary structure and wherein the heater-thermometer provides both heating and temperature sensing in a single element comprising said region of doped single crystal silicon; and
monitoring a temperature of the heater-thermometer.

15. The method of claim 14, further comprising a step of providing a compound to a surface of the single crystal silicon suspended structure.

16. The method of claim 14, further comprising a step of providing a current to the heater-thermometer to raise a temperature of the heater thermometer.

17. The method of claim 14 wherein the step of monitoring the temperature of the heater-thermometer comprises measuring a resistance of the heater-thermometer.

18. A method of determining the energy density of a combustible material, the method comprising:
providing a microcalorimeter comprising a single crystal silicon suspended structure supported by one or more single crystal silicon tethers, wherein the single crystal silicon suspended platform comprises a heater-thermometer, wherein the heater-thermometer comprises a region of doped single crystal silicon within the single crystal silicon suspended structure, wherein the single crystal silicon suspended structure and heater-thermometer comprise a unitary structure and wherein the heater-thermometer provides both heating and temperature sensing in a single element comprising said region of doped single crystal silicon;
providing a combustible material to a surface of the single crystal silicon suspended structure;
providing a current to the heater-thermometer to heat the heater-thermometer and the combustible material and initiate combustion of the combustible material; and
monitoring a temperature of the heater-thermometer.

19. The method of claim 18 wherein the step of monitoring the temperature of the heater-thermometer comprises measuring a resistance of the heater-thermometer.

* * * * *